US012675880B2

(12) United States Patent
Wang et al.

(10) Patent No.: US 12,675,880 B2
(45) Date of Patent: Jul. 7, 2026

(54) TRANSFORMATION OF HISTOCHEMICALLY STAINED IMAGES INTO SYNTHETIC IMMUNOHISTOCHEMISTRY (IHC) IMAGES

(71) Applicants: Ventana Medical Systems, Inc., Tucson, AZ (US); Genentech, Inc., South San Francisco, CA (US)

(72) Inventors: Xingwei Wang, Sunnyvale, CA (US); Auranuch Lorsakul, Santa Clara, CA (US); Zuo Zhao, Palo Alto, CA (US); Yao Nie, Sunnyvale, CA (US); Hartmut Koeppen, San Mateo, CA (US); Hauke Kolster, Fresno, CA (US); Kandavel Shanmugam, Oro Valley, AZ (US)

(73) Assignees: Ventana Medical Systems, Inc., Tucson, AZ (US); Genentech, Inc., South San Francisco, CA (US)

( * ) Notice: Subject to any disclaimer, the term of this patent is extended or adjusted under 35 U.S.C. 154(b) by 188 days.

(21) Appl. No.: 18/482,697

(22) Filed: Oct. 6, 2023

(65) Prior Publication Data

US 2024/0046473 A1 Feb. 8, 2024

Related U.S. Application Data

(63) Continuation of application No. PCT/US2022/024879, filed on Apr. 14, 2022.
(Continued)

(51) Int. Cl.
*G06T 7/00* (2017.01)
*G16H 30/40* (2018.01)

(52) U.S. Cl.
CPC .......... *G06T 7/0012* (2013.01); *G16H 30/40* (2018.01); *G06T 2207/20081* (2013.01); *G06T 2207/20084* (2013.01)

(58) Field of Classification Search
None
See application file for complete search history.

(56) References Cited

U.S. PATENT DOCUMENTS

2005/0202559 A1* 9/2005 Pownall ................. C12N 15/86
435/101
2014/0270457 A1 9/2014 Bhargava
(Continued)

FOREIGN PATENT DOCUMENTS

CA 3095739 A1 10/2019
CN 107851303 A 3/2018
(Continued)

OTHER PUBLICATIONS

"Pix2Pix: Image conversion using CGAN", Dec. 29, 2019, blog. negativemind.com/2019/12/29/pix2pix-image-to-image-translation-with-conditional-adversarial-networks.
(Continued)

*Primary Examiner* — Helen Zong
(74) *Attorney, Agent, or Firm* — Mughal Gaudry & Franklin PC

(57) ABSTRACT

The present disclosure relates to techniques for obtaining a synthetic immunohistochemistry (IHC) image from a histochemically stained image. Particularly, aspects of the present disclosure are directed to accessing an input image that depicts a tissue section that has been stained with at least one histochemical stain; generating a synthetic image by processing the input image using a trained generator network; and outputting the synthetic image. The synthetic image depicts a tissue section that has been stained with at least one IHC stain that targets a first antigen, and techniques may also
(Continued)

Tissue Slides — 110

100

Digital Scanner — 120

Image Analysis Algorithms — 130

Scoring — 140 include receiving an input that is based on a level of expression of a first antigen from the synthetic image and/or generating, from the synthetic image, a value that is based on a level of expression of the first antigen.

23 Claims, 20 Drawing Sheets
(13 of 20 Drawing Sheet(s) Filed in Color)

Related U.S. Application Data

(60) Provisional application No. 63/174,981, filed on Apr. 14, 2021.

(56) References Cited

U.S. PATENT DOCUMENTS

| | | | |
|---|---|---|---|
| 2016/0237397 A1* | 8/2016 | Guia | C12M 47/04 |
| 2018/0112277 A1* | 4/2018 | Krizman | A61K 39/39558 |
| 2021/0005308 A1 | 1/2021 | Klaiman | |
| 2024/0135544 A1 | 4/2024 | Ozcan et al. | |
| 2025/0046069 A1* | 2/2025 | Ozcan | G06V 10/82 |
| 2025/0232443 A1* | 7/2025 | Freytag | G06T 7/0014 |

FOREIGN PATENT DOCUMENTS

| | | |
|---|---|---|
| CN | 111602136 A | 8/2020 |
| JP | 2021519924 A | 8/2021 |
| WO | 2019122047 A1 | 6/2019 |
| WO | 2019139591 A1 | 7/2019 |

OTHER PUBLICATIONS

Burlingname, Erik A. "SHIFT: speedy histopathological-to-immuno fluorescent translation of whole slide images using conditional generative adversarial networks". Progress in Biomedical Optics and Imaging, SPIE—International Society for Optical Engineering, vol. 10581, Mar. 6, 2018, pp. 1058105-1-1058105-7.

Notice of Reasons for Rejection in Japanese Patent Application No. 2023-562767, dated Dec. 24, 2024.

Qiita, "The Advent of pix2pix—Verification Part 2: Understanding the U-net structure—", Feb. 22, 2018, qiita.com/MuAuan/items/387cca897fab12f1b6a5.

Communication pursuant to Article 94(3) EPC for European Patent Application No. 22725948.8, dated Oct. 30, 2025.

Decision to Grant a Patent in Japanese Patent Application No. 2023-562767, dated Aug. 12, 2025.

De Haan et al., "Deep Learning-based transformation of the H&E stain into special stains", Cornell University Library, Aug. 2020.

International Search Report and Written Opinion for PCT Application No. PCT/US2022/024879, dated Sep. 19, 2022.

Isola, P., "Image-to-Image Translation with Conditional Adversarial Networks", CVPR 2017.

Liu, Shuting et al. "Unpaired Stain Transfer Using Pathology-Consistent Constrained Generative Adversarial Networks", IEEE Transactions on Medical Imaging, vol. 40, No. 8, 2021.

Wolff, A. et al., "Human Epidermal Growth Factor Receptor 2 Testing in Breast Cancer: American Society of Clinical Oncology/College of American Pathologists Clinical Practice Guideline Focused Update", Journal of Clinical Oncology, vol. 36, No. 20, Jul. 10, 2018.

Lahiani, A. et al. "Perceptual Embedding Consistency for Seamless Reconstruction of Tilewise Style Transfer", arXiv:1906.00617v1, Jun. 3, 2019.

Office Action for Chinese Patent Application No. 202280040547.7, dated Apr. 16, 2026.

Xu, Z. et al., "GAN-based Virtual Re-Staining: A Promising Solution for Whole Slide Image Analysis", arXiv:1901.04059v1, Jan. 13, 2019.

* cited by examiner

FIG. 1

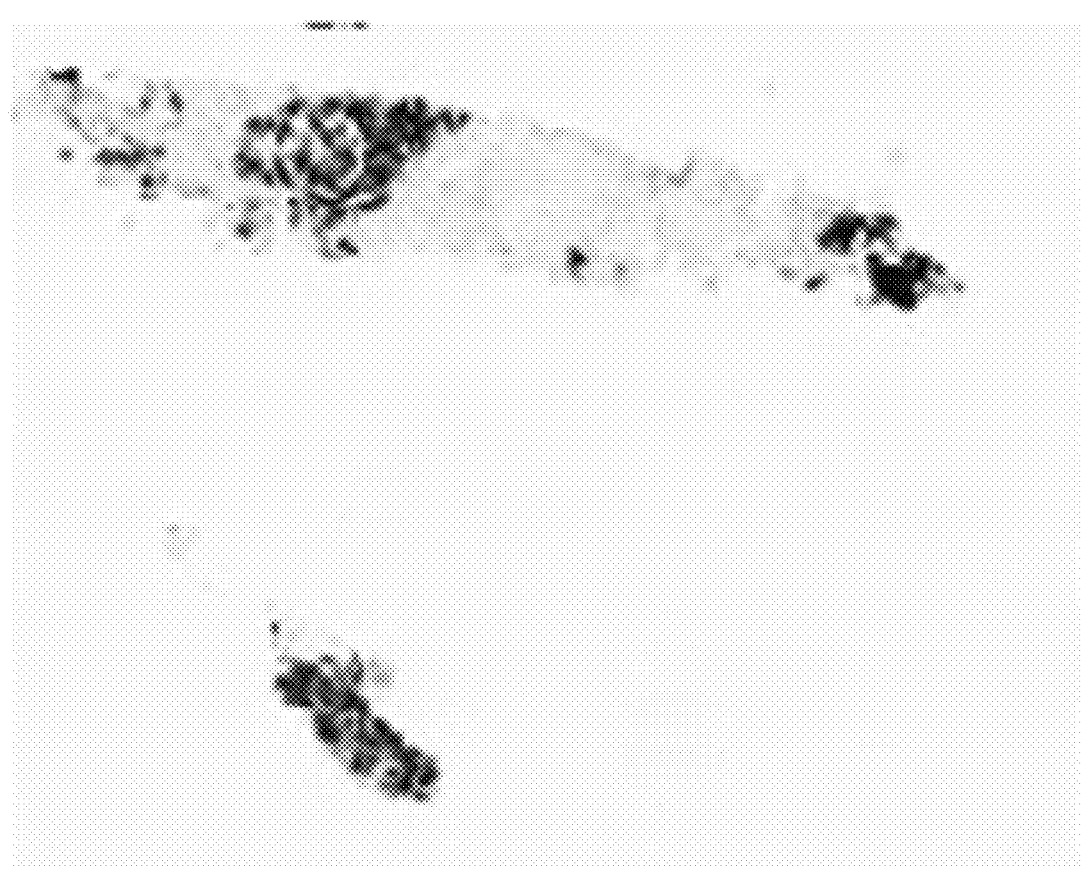
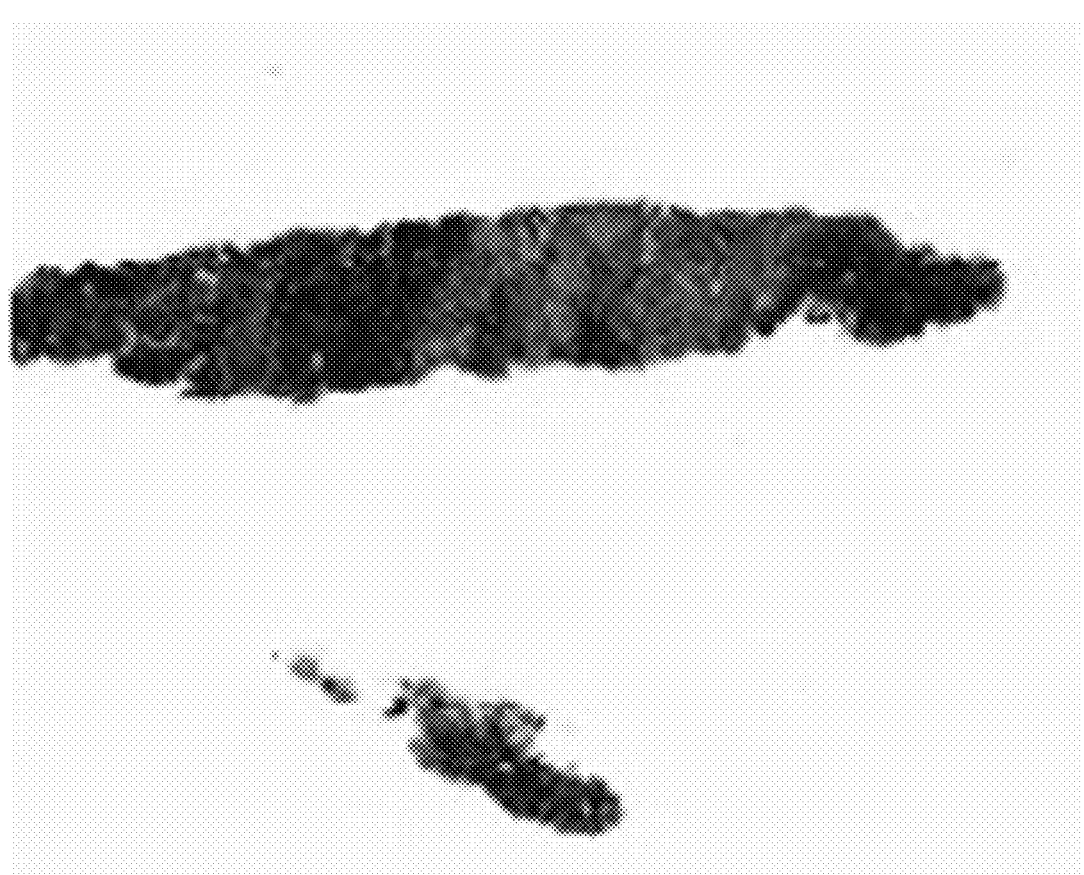
FIG. 2

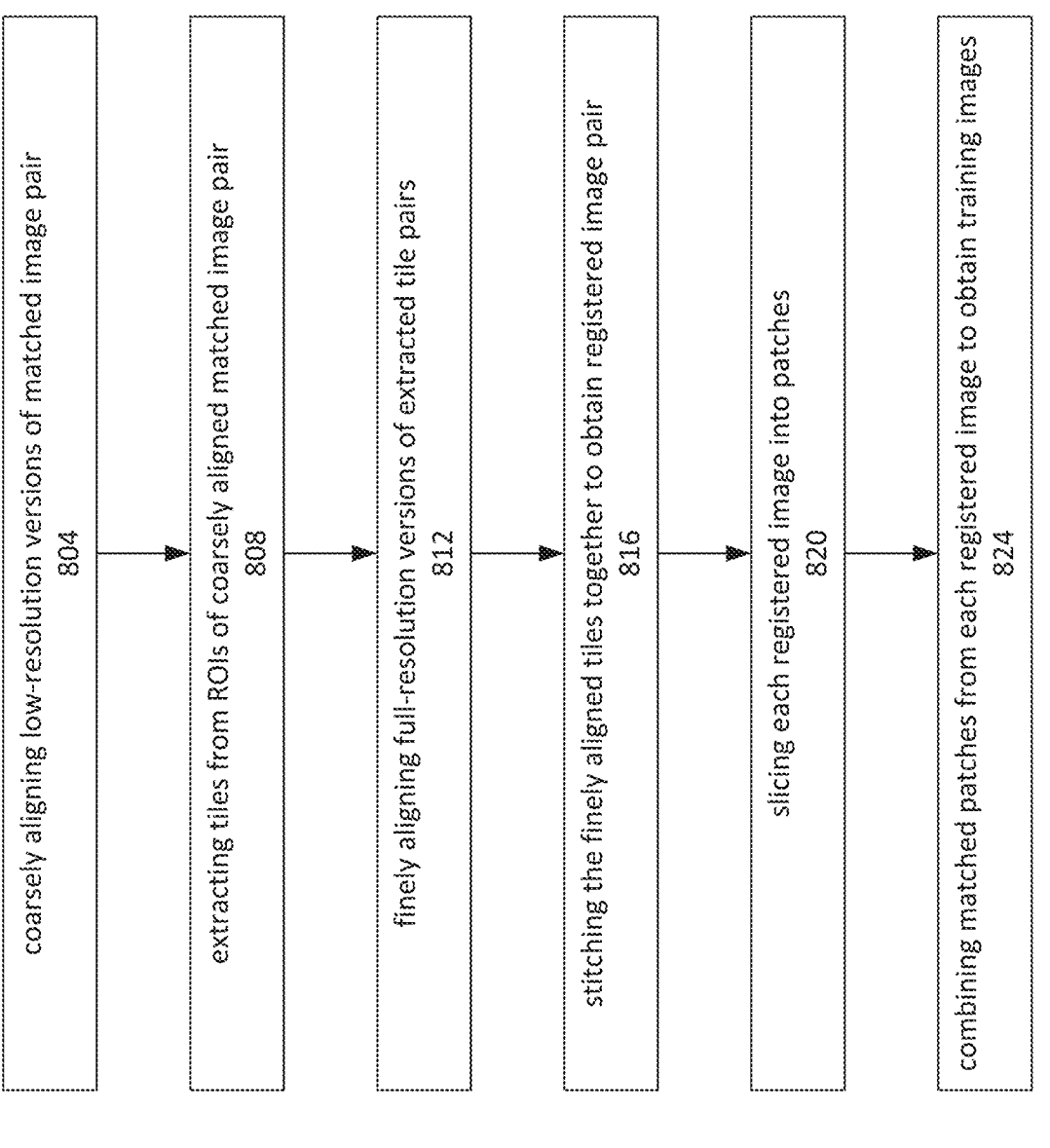

800 coarsely aligning low-resolution versions of matched image pair
804 extracting tiles from ROIs of coarsely aligned matched image pair
808 finely aligning full-resolution versions of extracted tile pairs
812 stitching the finely aligned tiles together to obtain registered image pair
816 slicing each registered image into patches
820 combining matched patches from each registered image to obtain training images
824

FIG. 8

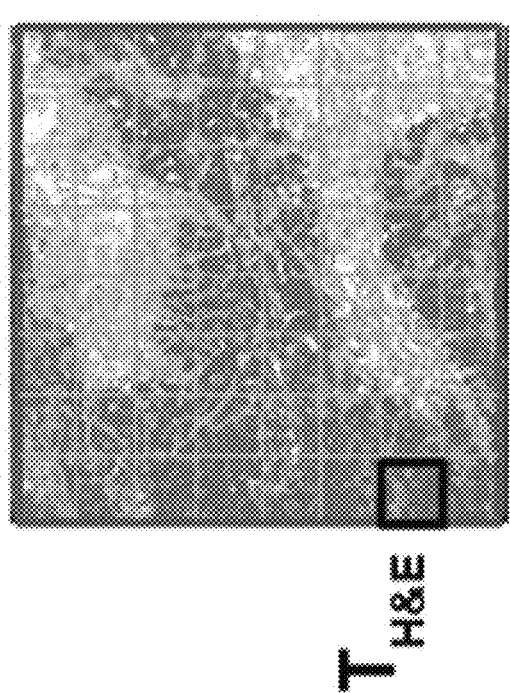
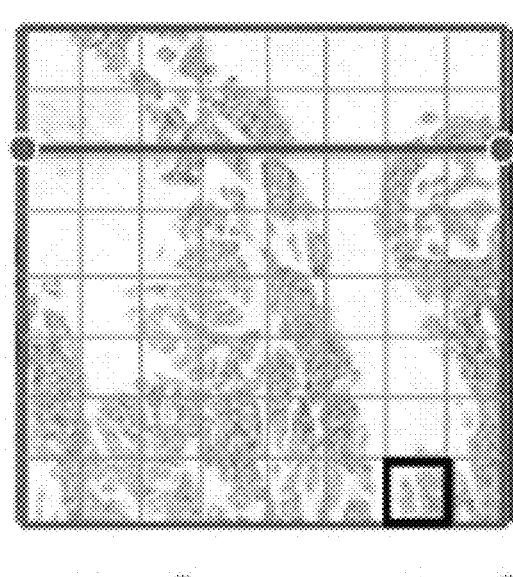
$P_{H\&E}$
$T_{H\&E}$
$P_{IHC}$
(2048x2048)
$T_{IHC}$
(256x256)
FIG. 10 accessing an input image that depicts a tissue section which has been stained with at least one histochemical stain
1504 generating a synthetic image by processing the input image using a generator network
1512 outputting the synthetic image
1516 generating a value that is based on the level of expression indicated by the synthetic image
1524

1502

FIG. 15B accessing an input image that depicts a tissue section which has been stained with at least one histochemical stain
1504 generating a synthetic image by processing the input image using a generator network
1512 outputting the synthetic image
1516 receiving an input that is based on the level of expression indicated by the synthetic image
1520

target output input

2+ (128 x 128)

target output input

2+ (256 x 256)

1+ (128 x 128)

1+ (256 x 256)

TRANSFORMATION OF HISTOCHEMICALLY STAINED IMAGES INTO SYNTHETIC IMMUNOHISTOCHEMISTRY (IHC) IMAGES

CLAIM OF PRIORITY

This Application is a Continuation of, and claim the benefit of priority to, PCT Patent Application No. PCT/US2022/024879, filed on Apr. 14, 2022, and titled "TRANSFORMATION OF HISTOCHEMICALLY STAINED IMAGES INTO SYNTHETIC IMMUNOHISTOCHEMISTRY (IHC) IMAGES", which claim priority to U.S. Provisional Application No. 63/174,981, filed on Apr. 14, 2021, both of which are incorporated by reference in their entireties for all purposes.

FIELD

The present disclosure relates to digital pathology, and in particular to techniques that include obtaining a synthetic immunohistochemistry (IHC) image from a histochemically stained image.

BACKGROUND

Histopathology may include examination of slides prepared from sections of tissue for a variety of reasons, such as: diagnosis of disease, assessment of a response to therapy, and/or the development of pharmacological agents to fight disease. Because the tissue sections and the cells within them are virtually transparent, preparation of the slides typically includes staining the tissue sections in order to render relevant structures more visible. Digital pathology may include scanning of the stained slides to obtain digital images, which may be subsequently examined by digital pathology image analysis and/or interpreted by a human pathologist.

Some types of tissue stains are highly specific and attach only to particular proteins (e.g., antigens), whose presence in a sample may indicate a particular condition (e.g., a particular type of cancer). While these stains can provide information that is essential for diagnosis, they are typically extremely expensive and require complex laboratory equipment and procedures. Other types of tissue stains that are less costly and more widely available can provide important general information about a sample, such as visual contrast between different structures within cells and/or tissues in a sample, but it has not been possible to use such stains to perform diagnoses based on antigen-specific detections.

SUMMARY

In various embodiments, a computer-implemented method of image transformation is provided that includes accessing an input image that depicts a tissue section that has been stained with at least one histochemical stain; generating a synthetic image by processing the input image using a generator network, the generator network having been trained using a training data set that includes a plurality of pairs of images; outputting the synthetic image; and receiving an input that is based on a level of expression of a first antigen from the synthetic image, where the synthetic image depicts a tissue section that has been stained with at least one immunohistochemical stain (IHC stain) that targets the first antigen, and where each pair of images of the plurality of pairs of images includes an image of a first section of a tissue that has been stained with the at least one histochemical stain and an image of a second section of the tissue that has been stained with the at least one IHC stain.

In some embodiments, the method includes determining, from the synthetic image, a value that is based on the level of expression of the first antigen. The determining may be performed, for example, by a trained network.

In various embodiments, a computer-implemented method of image transformation is provided that includes accessing an input image that depicts a tissue section that has been stained with at least one histochemical stain; generating a synthetic image by processing the input image using a generator network, the generator network having been trained using a training data set that includes a plurality of pairs of images; outputting the synthetic image; and receiving an input that is based on a level of expression of a first antigen from the synthetic image, where the synthetic image depicts a tissue section that has been stained with at least one IHC stain that targets the first antigen, and where each pair of images of the plurality of pairs of images includes an image of a first section of a tissue that has been stained with the at least one histochemical stain and an image of a second section of the tissue that has been stained with the at least one IHC stain.

In some embodiments, the histochemical stain is hematoxylin and eosin.

In some embodiments, the first antigen is a tumor-associated antigen. For example, the first antigen may be human epidermal growth receptor 2 (HER2). In such case, the received input value and/or the generated value may be a HER2 score.

In some embodiments, the generator network was trained as part of a generative adversarial network.

In some embodiments, for each pair of images of the plurality of pairs of images, the image of the first section is stitched to the image of the second section. In such case, for each pair of images of the plurality of pairs of images, the image of the first section may be registered with the image of the second section before being stitched to the image of the second section.

In some embodiments, the computer-implemented method further comprises determining, by a user, a diagnosis of a subject based on the synthetic image.

In some embodiments, the computer-implemented method further comprises administering, by the user, a treatment with a compound based on (i) the synthetic image, and/or (ii) the diagnosis of the subject.

In some embodiments, a system is provided that includes one or more data processors and a non-transitory computer readable storage medium containing instructions which, when executed on the one or more data processors, cause the one or more data processors to perform part or all of one or more methods disclosed herein.

In some embodiments, a computer-program product is provided that is tangibly embodied in a non-transitory machine-readable storage medium and that includes instructions configured to cause one or more data processors to perform part or all of one or more methods disclosed herein.

Some embodiments of the present disclosure include a system including one or more data processors. In some embodiments, the system includes a non-transitory computer readable storage medium containing instructions which, when executed on the one or more data processors, cause the one or more data processors to perform part or all of one or more methods and/or part or all of one or more processes disclosed herein. Some embodiments of the present disclosure include a computer-program product tangibly embodied in a non-transitory machine-readable storage medium, including instructions configured to cause one or more data processors to perform part or all of one or more methods and/or part or all of one or more processes disclosed herein.

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention as claimed has been specifically disclosed by embodiments and optional features, modification and variation of the concepts herein disclosed may be resorted to by those skilled in the art, and that such modifications and variations are considered to be within the scope of this invention as defined by the appended claim.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Aspects and features of the various embodiments will be more apparent by describing examples with reference to the accompanying drawings, in which:

FIG. 1 shows an example diagram of a digital pathology solution workflow;

FIG. 2 shows an example of paired hematoxylin-eosin (H&E) and human epidermal growth factor 2 (HER2)-immunohistochemistry (IHC) images;

FIG. 8 illustrates a flowchart for an exemplary process according to some embodiments;

FIG. 10 shows an example of extraction of tiles from whole slide images according to some embodiments;

FIG. 15A illustrates a flowchart for an exemplary process according to some embodiments;

FIG. 15B illustrates a flowchart for another exemplary process according to some embodiments;

FIG. 16 shows an example of sets of training data according to some embodiments.

DETAILED DESCRIPTION

Figure 3:
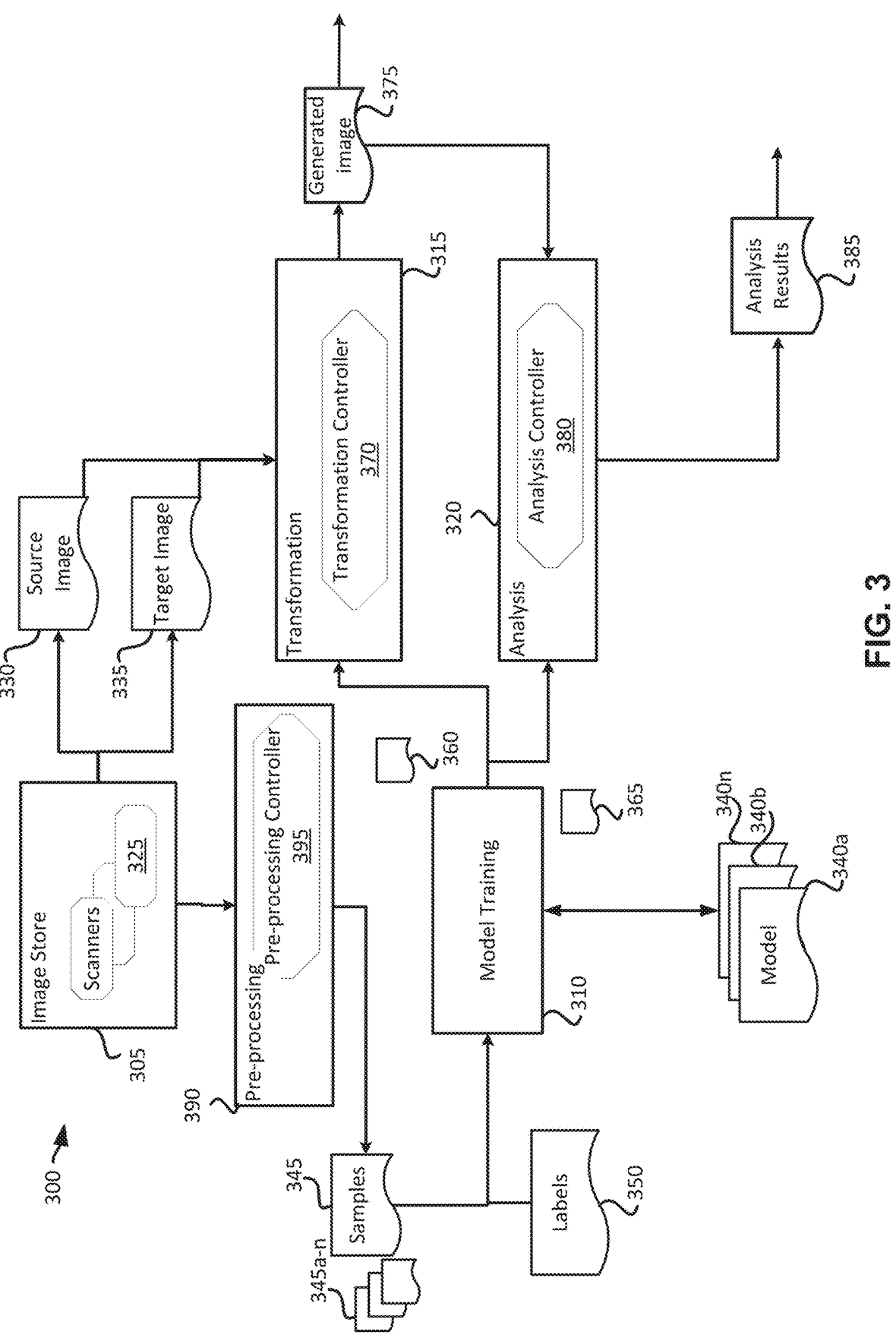
FIG. 3 illustrates an example computing environment according to some embodiments.

Systems, methods and software disclosed herein facilitate obtaining synthetic IHC images from histochemically stained images. While certain embodiments are described, these embodiments are presented by way of example only, and are not intended to limit the scope of protection. The apparatuses, methods, and systems described herein may be embodied in a variety of other forms. Furthermore, various omissions, substitutions, and changes in the form of the example methods and systems described herein may be made without departing from the scope of protection.

I. Overview

Figure 1:
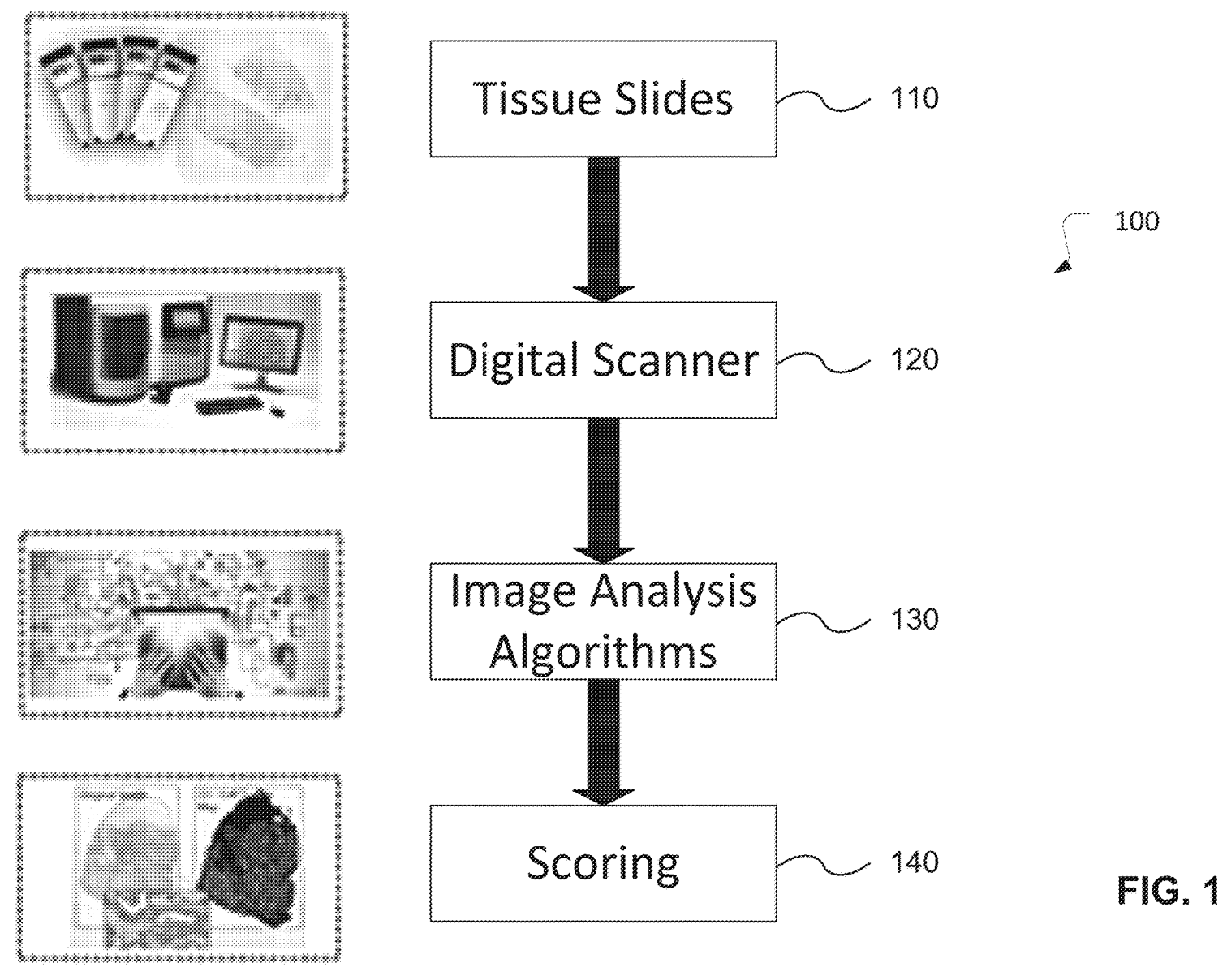

Digital pathology may involve the interpretation of digitized images in order to correctly diagnose subjects and guide therapeutic decision making. In digital pathology solutions, image-analysis workflows can be established to automatically detect or classify biological objects of interest e.g., positive, negative tumor cells, etc. FIG. 1 shows an example diagram of a digital pathology solution workflow 100. The digital pathology solution workflow 100 includes obtaining tissue slides at block 105, scanning preselected areas or the entirety of the tissue slides with a digital image scanner (e.g., a whole slide image (WSI) scanner) to obtain digital images at block 110, performing image analysis on the digital image using one or more image analysis algorithms at block 115, and scoring objects of interest based on the image analysis (e.g., quantitative or semi-quantitative scoring such as positive, negative, medium, weak, etc.).

Evaluation of tissue changes caused, for example, by disease, may be performed by examining thin tissue sections. A tissue sample (e.g., a sample of a tumor) may be sliced to obtain a series of sections, with each section having a thickness of, for example, 4-5 microns. Because the tissue sections and the cells within them are virtually transparent, preparation of the slides typically includes staining the tissue sections in order to render relevant structures more visible. For example, different sections of the tissue may be stained with one or more different stains to express different characteristics of the tissue.

Each section may be mounted on a slide, which is then scanned to create a digital image that may be subsequently examined by digital pathology image analysis and/or interpreted by a human pathologist (e.g., using image viewer software). The pathologist may review and manually annotate the digital image of the slides (e.g., tumor area, necrosis, etc.) to enable the use of image analysis algorithms to extract meaningful quantitative measures (e.g., to detect and classify biological objects of interest). Conventionally, the pathologist may manually annotate each successive image of multiple tissue sections from a tissue sample to identify the same aspects on each successive tissue section.

One type of tissue staining is histochemical staining, which uses one or more chemical dyes (e.g., acidic dyes, basic dyes) to stain tissue structures. Histochemical staining may be used to indicate general aspects of tissue morphology and/or cell microanatomy (e.g., to distinguish cell nuclei from cytoplasm, to indicate lipid droplets, etc.). One example of a histochemical stain is hematoxylin and eosin (H&E). Other examples of histochemical stains include trichrome stains (e.g., Masson's Trichrome), Periodic Acid- Schiff (PAS), silver stains, and iron stains. The molecular weight of a histochemical staining reagent (e.g., dye) is typically about 500 kilodaltons (kD) or less, although some histochemical staining reagents (e.g., Alcian Blue, phosphomolybdic acid (PMA)) may have molecular weights of up to two or three thousand kD. One case of a high-molecular-weight histochemical staining reagent is alpha-amylase (about 55 kD), which may be used to indicate glycogen.

Another type of tissue staining is immunohistochemistry (IHC, also called "immunostaining"), which uses a primary antibody that binds specifically to the target antigen of interest (also called a biomarker). IHC may be direct or indirect. In direct IHC, the primary antibody is directly conjugated to a label (e.g., a chromophore or fluorophore). In indirect IHC, the primary antibody is first bound to the target antigen, and then a secondary antibody that is conjugated with a label (e.g., a chromophore or fluorophore) is bound to the primary antibody. The use of IHC for tissue staining typically requires the use of very expensive reagents and more complicated laboratory equipment and procedures than histochemical staining. The molecular weights of IHC reagents are much higher than those of histochemical staining reagents, as the antibodies have molecular weights of about 150 kD or more.

The level of expression of the human epidermal growth factor receptor 2 (HER2) biomarker in a tumor is an important biomarker for diagnosis of several types of cancers, including breast cancer. Whether and how strongly a tumor is HER2-positive (HER2+) or HER2-negative (HER2−) may indicate whether a particular drug or other therapy is likely to be effective at treating the cancer. The following criteria are used to assign a HER2 score to a slide of a section of a tumor sample that has been HER2-IHC-stained:

| | |
|---|---|
| IHC 0 | No staining or incomplete, barely perceptible membrane staining in 10% of tumor cells or less. |
| IHC 1+ | Incomplete, barely perceptible membrane staining in more than 10% of tumor cells. |
| IHC 2+ | Weak to moderate complete membrane staining in more than 10% of tumor cells. |
| IHC 3+ | Circumferential, complete, intense membrane staining in more than 10% of tumor cells. |

The current practice to diagnose HER2+ breast cancer commonly relies on pathological evaluation of slides of H&E-stained samples and of multiple slides of IHC-stained samples. To confirm a breast cancer diagnosis, preparation of extra multiple tissue sections for HER2-IHC slides is typically required. FIG. 2 shows an example of an image of a section of a tumor sample that has been H&E-stained (left) and an image of a nearby section of the same tumor sample that has been HER2-IHC-stained (right). Preparation of multiple stained images can be labor intensive and incurs extra cost. In addition, it requires pathologists to review additional tissue slides and annotations.

In many diagnostic scenarios (e.g., in cancer diagnosis), it is typical that an H&E-stained sample is prepared for every subject, as preparing such a sample is routine and easy, widely practiced and available, and inexpensive. The hematoxylin stains the cell nuclei blue, while eosin stains the extracellular matrix and cytoplasm pink, and other structures may be stained to have different shades, hues, and/or combinations of pink and blue. While the H&E stain is useful for identifying general tissue and cell anatomy, however, it fails to provide the specific information needed to support certain diagnostic evaluations, such as distinguishing between different types of cancer (e.g., HER2 scoring), which may be provided by IHC.

In order to overcome these limitations as well as others, techniques are disclosed herein for generating, from an image of a histochemically stained sample (e.g., an H&E stained sample), a synthetic image that depicts an IHC-stained sample. Generation of such a synthetic image may support evaluation of the level of expression of a biomarker in the sample without the need to prepare and image a corresponding IHC-stained sample.

Generation of the synthetic image may be performed by a trained generator network, which may include parameters learned while training a Generative Adversarial Network (GAN). The GAN may further include a discriminator network configured to predict whether an input image is fake (i.e., has been generated by the generator network) or real (i.e., depicts an actual image collected from a subject). Feedback based on the accuracy of these predictions can be provided to the generator network during training.

One illustrative embodiment of the present disclosure is directed to a method of image transformation that includes accessing an input image that depicts a tissue section that has been stained with at least one histochemical stain; generating a synthetic image by processing the input image using a generator network, outputting the synthetic image; and receiving an input that is based on a level of expression of a first antigen from the synthetic image, where the synthetic image depicts a tissue section that has been stained with at least one IHC stain that targets the first antigen, and where the generator network has been trained using a training data set that includes a plurality of pairs of images, and where each pair of images of the plurality of pairs of images includes an image of a first section of a tissue that has been stained with the at least one histochemical stain and an image of a second section of the tissue that has been stained with the at least one IHC stain.

Another illustrative embodiment of the present disclosure is directed to a method of image transformation that includes accessing an input image that depicts a tissue section that has been stained with at least one histochemical stain; generating a synthetic image by processing the input image using a generator network, outputting the synthetic image; and generating, from the synthetic image, a value that is based on a level of expression of a first antigen, where the synthetic image depicts a tissue section that has been stained with at least one IHC stain that targets the first antigen, and where the generator network has been trained using a training data set that includes a plurality of pairs of images, and where each pair of images of the plurality of pairs of images includes an image of a first section of a tissue that has been stained with the at least one histochemical stain and an image of a second section of the tissue that has been stained with the at least one IHC stain.

Advantageously, a method of image transformation as described herein enables use of H&E and synthetic IHC data to assist a pathologist in the efficient diagnosis of a cancer (e.g., breast cancer) subtype. Such a method may be implemented as a key part of a fast screening process that may be used, for example, to identify subjects who have HER2 3+ tumors (e.g., among subjects with breast cancer) without performing an actual IHC staining. Moreover, such "virtual staining" technology can also be combined with other artificial intelligence (AI) technologies to enhance the authenticity of the AI system (e.g., to enhance explainability and truthfulness of the algorithm output). Even further, a method of image transformation as described herein may be used to generate a large amount of imaging data (e.g., a large number of synthetic HER2-IHC images) for algorithm verification and training, thereby reducing the cost and time of algorithm development.

II. Definitions

As used herein, when an action is "based on" something, this means the action is based at least in part on at least a part of the something.

As used herein, the terms "substantially," "approximately" and "about" are defined as being largely but not necessarily wholly what is specified (and include wholly what is specified) as understood by one of ordinary skill in the art. In any disclosed embodiment, the term "substantially," "approximately," or "about" may be substituted with "within [a percentage] of" what is specified, where the percentage includes 0.1, 1, 5, and 10 percent.

As used herein, the term "sample" "biological sample" or "tissue sample" refers to any sample including a biomolecule (such as a protein, a peptide, a nucleic acid, a lipid, a carbohydrate, or a combination thereof) that is obtained from any organism including viruses. Other examples of organisms include mammals (such as humans; veterinary animals like cats, dogs, horses, cattle, and swine; and laboratory animals like mice, rats and primates), insects, annelids, arachnids, marsupials, reptiles, amphibians, bacteria, and fungi. Biological samples include tissue samples (such as tissue sections and needle biopsies of tissue), cell samples (such as cytological smears such as Pap smears or blood smears or samples of cells obtained by microdissection), or cell fractions, fragments or organelles (such as obtained by lysing cells and separating their components by centrifugation or otherwise). Other examples of biological samples include blood, serum, urine, semen, fecal matter, cerebrospinal fluid, interstitial fluid, mucous, tears, sweat, pus, biopsied tissue (for example, obtained by a surgical biopsy or a needle biopsy), nipple aspirates, cerumen, milk, vaginal fluid, saliva, swabs (such as buccal swabs), or any material containing biomolecules that is derived from a first biological sample. In certain embodiments, the term "biological sample" as used herein refers to a sample (such as a homogenized or liquefied sample) prepared from a tumor or a portion thereof obtained from a subject.

III. Techniques for Digital Pathology Image Transformation

Reliable results are important to the availability of cancer therapies, such as HER2 target therapies. In pathology it is known, for example, that HER2-IHC is susceptible to preanalytical variables. In one application of the techniques described herein, images of H&E slides and synthetic IHC images derived from those images are used to support diagnosis and immunotherapy for breast cancer, by using the generated synthetic IHC images to predict HER2 scores/stain intensity levels.

FIG. 3 illustrates an example computing environment 300 (i.e., a data processing system) for transforming an input image that depicts a tissue section that has been stained with at least one histochemical stain into a synthetic image that depicts a tissue section that has been stained with at least one IHC stain according to various embodiments. As shown in FIG. 3, the transforming of the input image performed by the computing environment 300 in this example includes several stages: an image store stage 305, an pre-processing stage 390, a model training stage 310, a transformation stage 315, and an analysis stage 320. The image store stage 310 may include one or more digital image scanners or databases 325 that are accessed (e.g., by pre-processing stage 390) to provide a source set of digital images 330 and a target set of digital images 335 from preselected areas or the entirety of the biological sample slides (e.g., tissue slides).

The model training stage 310 builds and trains one or more models 340a-340n ('n' represents any natural number) (which may be referred to herein individually as a model 340 or collectively as the models 340) to be used by the other stages. The model 340 can be a machine-learning ("ML") model, which may include a convolutional neural network ("CNN"), an inception neural network, a residual neural network ("Resnet"), a U-Net, a V-Net, a single shot multibox detector ("SSD") network, a recurrent neural network ("RNN"), a deep neural network, a rectified linear unit ("ReLU"), a long short-term memory ("LSTM") model, a gated recurrent units ("GRUs") model, the like, or any combination thereof. In various embodiments, a generative model is configured with parameters that were learned by training a model 340 that is capable of learning any kind of data distribution using unsupervised learning, such as a Generative Adversarial Network ("GAN"), a deep convolutional generative adversarial network ("DCGAN"), variation autoencoders (VAEs), a hidden Markov model ("HMM"), Gaussian mixture model, Boltzmann machine, the like, or combinations of one or more of such techniques—e.g., VAE-GAN. The computing environment 300 may employ the same type of model or different types of models for transforming source images into generated images. In certain instances, the generative model is configured with parameters that were learned by training a model 340 that is a GAN constructed with a loss function that tries to classify if the output image is real or fake, while simultaneously training a generative model to minimize this loss.

Figure 4:
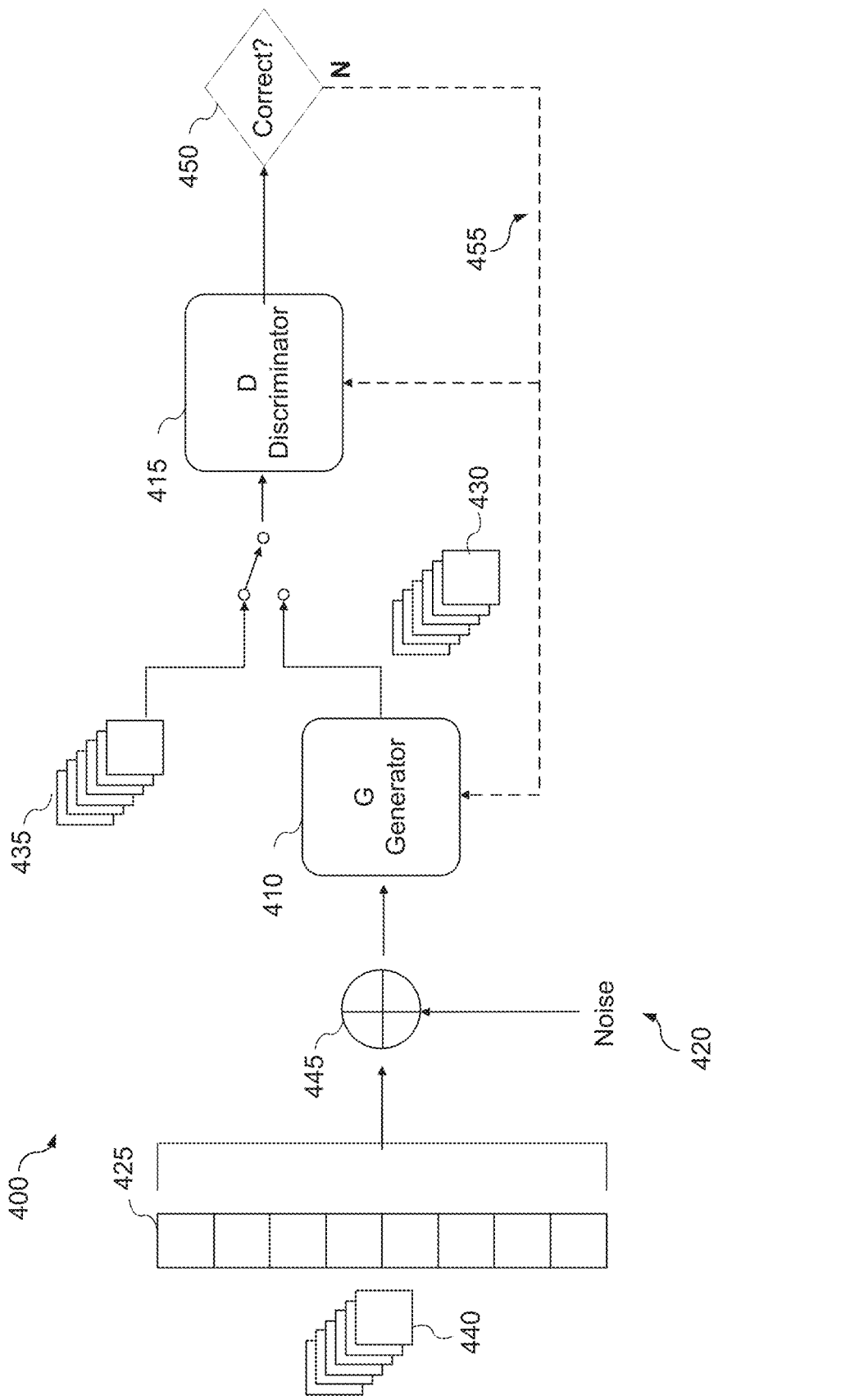
FIG. 4 illustrates an conditional GAN model according to some embodiments.

In an exemplary embodiment shown in FIG. 4, the model 340 that is trained to provide the learned parameters is a conditional GAN ("cGAN") 400, which is an extension of the GAN model, and generates images that have certain conditions or attributes. A cGAN learns a structured loss that penalizes the joint configuration of the output. Referring to FIG. 4, the cGAN 400 includes a generator 410 and a discriminator 415. The generator 410 is a neural network (e.g., a CNN) that takes a randomly generated noise vector 420 and a latent feature vector (or a one-dimensional vector) 425 (the condition, e.g., in the present instance, the source image) as input data and feedback from the discriminator 415 and generates new images 430 that are as close to real target images 435 as possible. The discriminator 415 is a neural network (e.g., a CNN) configured as a classifier to determine whether the generated image 430 from the generator 410 is a real image or a fake image. The latent feature vector 425 or the condition is derived from a source image or set of source images 440 (e.g., images from one or more digital scanners, from an image server, etc.), which encode the class (e.g., images that have been histochemically stained) or a set of specific characteristics expected from the source image 440. The randomly generated noise vector 420 may be generated from a Gaussian distribution, and the vector space may be comprised of latent variables or hidden variables that are important for the domain but not directly observable. The latent feature vector 425 and the random noise vector 420 may be combined as input 445 to the generator 410. Alternatively or additionally, the noise may be added within the generator 410 in the form of dropouts (e.g., probabilistically dropping inputs to a layer).

The generator 410 receives the combined input 445 and generates the image 430 based on the latent feature vector 425 and the random noise vector 420 in the problem domain (i.e., domain of characteristics associated with target images 435 that have been IHC-stained). The discriminator 415 performs conditional-image classification by taking both a target image 435 and a generated image 430 as input and predicts 450 the likelihood of whether the generated image 430 is real or a fake translation of the target image 435. The output of discriminator 415 depends on the size of the generated image 430 but may be one value or a square activation map of values. Each value is a probability for the likelihood that a patch in the generated image 430 is real. These values can be averaged to give an overall likelihood or classification score if needed. The loss function of both the generator 410 and discriminator 415 may be configured such that the loss is dependent on how well the discriminator 415 performs its job of predicting 450 the likelihood of whether generated image 430 is real or a fake translation of the target image 435. After sufficient training, the generator 410 will begin to produce generated images 430 that look more like the target images 435. Training of the GAN 400 may proceed for a predefined number of training instances, and the resulting learned parameters may be accepted so long as one or more performance metrics (e.g., accuracy, precision and/or recall) determined using a training or validation set exceed corresponding thresholds. Alternatively, training of the GAN 400 may proceed until one or more performance metrics associated with recent training iterations exceed corresponding thresholds. At this point, the generated images 430 may be sufficiently similar to the target images 435 that the discriminator is no longer able to discern real from fake. Once the generator network 410 has been trained, a source set of images obtained from slides that have been histochemically stained (e.g., H&E-stained) may be input into the GAN 400 to transform the source set of images into a new generated set of images with their characteristics similar to a target set of images obtained from slides that have been immunostained (e.g., HER2-IHC-stained). Thereafter, the new generated set of images can be evaluated by a pathologist (e.g., to determine a HER2 score), analyzed using currently available computerized digital pathology image analysis algorithms, and/or used as input to train and/or verify a further network, etc.

With reference back to FIG. 3, to train model 340 in this example, pre-processing stage 390 generates samples 345 by obtaining digital images (a source set of digital images 330 and a target set of digital images 335), splitting the images into pairwise subsets of images 345a (at least one pair of a source image and a target image) for training (e.g., 90%) and pairwise subsets of images 345b for validation (e.g., 10%), preprocessing the pairwise subsets of images 345a and the pairwise subset of images 345b, augmenting the pairwise subset of images 345a, and possibly in some instances annotating the pairwise subset of images 345a with labels 350. The pairwise subset of images 345a may be obtained, for example, from a data storage structure such as a database or image server. Each image depicts a biological sample such as tissue.

The splitting may be performed randomly or pseudo-randomly (e.g., using a 90%/10%, 80%/20%, or 70%/30%) or the splitting may be performed in accordance with a more complex validation technique such as K-Fold Cross-Validation, Leave-one-out Cross-Validation, Leave-one-group-out Cross-Validation, Nested Cross-Validation, or the like to minimize sampling bias and overfitting. The preprocessing may comprise cropping the images such that each image only contains a single object of interest. In some instances, the preprocessing may further comprise standardization or normalization to put all features on a same scale (e.g., a same size scale or a same color scale or color saturation scale). In certain instances, the images are resized with a minimum size (width or height) of predetermined pixels (e.g., 2500 pixels) or with a maximum size (width or height) of predetermined pixels (e.g., 3000 pixels) and kept with the original aspect ratio.

Figure 5:
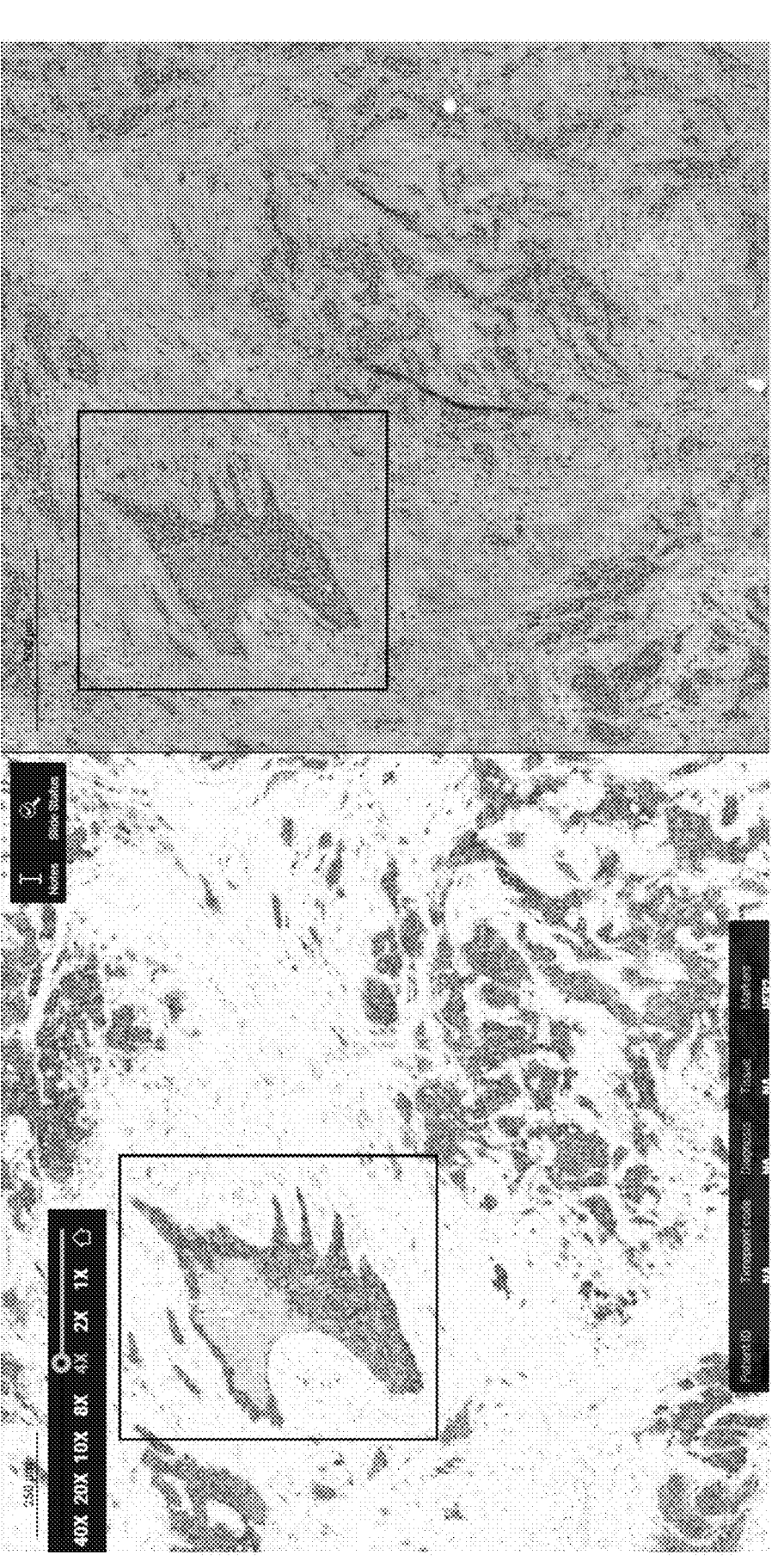
FIG. 5 shows an example of a matched pair of an H&E image and a HER2-IHC image.

For example, pre-processing stage 390 may prepare multiple patched images from a source set and a target set as one or more pairwise subsets of images for training data. The preparation of the paired images may comprise accessing matched pairs of a source image and a target image, in which the source image and the target image are from slides of nearby sections of the same biological sample (e.g., a tumor sample), the section in the source image has been stained with one or more selected histochemical stains, and the section in the target image has been stained with one or more selected IHC stains. In one non-limiting example, the sections in each of the source images have been stained with H&E, and the sections in each of the target images have been stained with HER2-IHC. FIG. 5 shows one example of a matched pair of an image of a HER2-IHC-stained slide (left) and an image of an H&E-stained slide (right).

Figure 6:
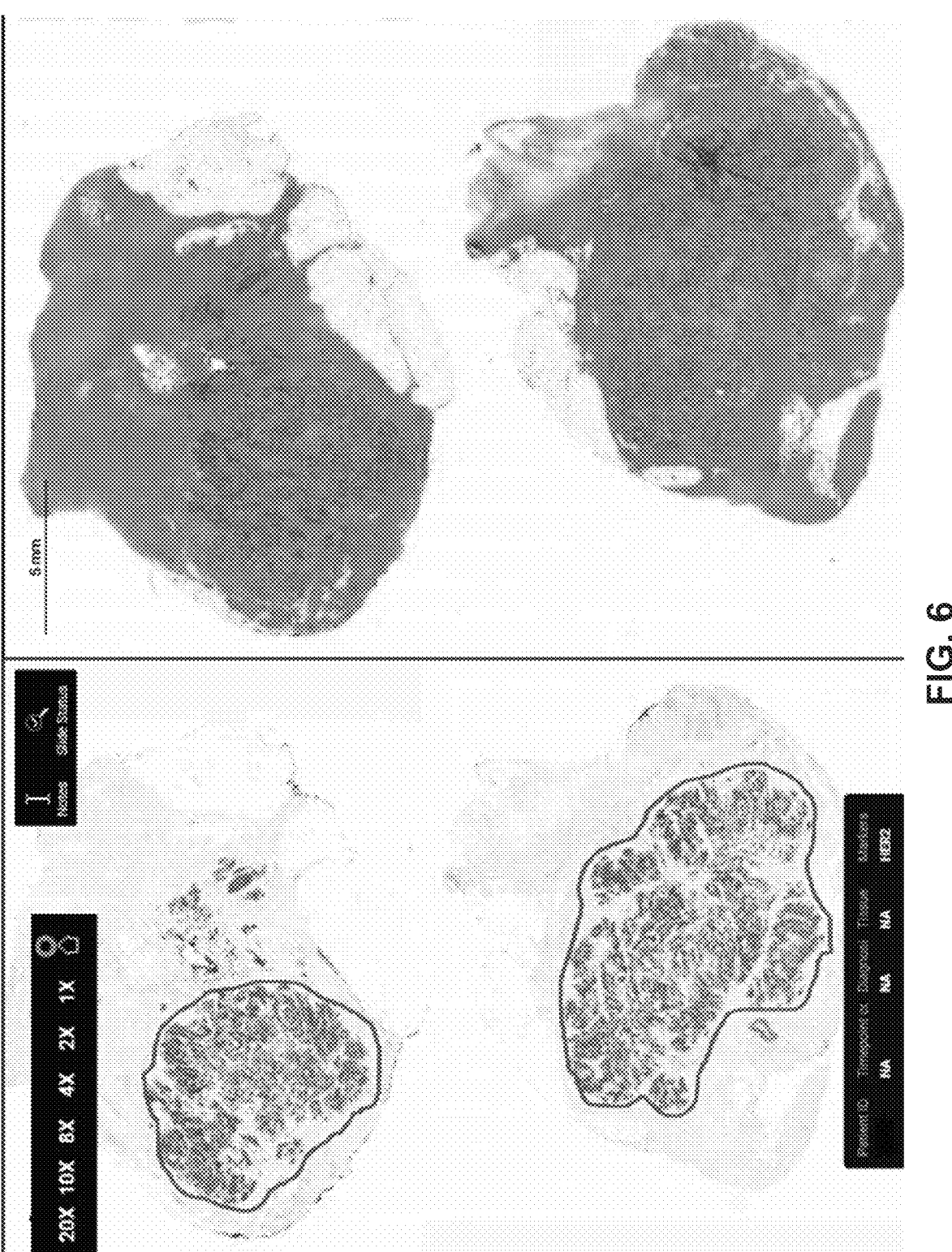
FIG. 6 shows examples of tumor annotations in HER2-IHC images.

Pre-processing stage 390 may then divide each of the paired images (e.g., whole slide images) into a number of patches of a predetermined size (e.g., 128×128, 256×256, or another size) to produce matched pairs of patches for training. It may be desired to use only patches that are from regions of interest within the images, such as tumor annotations that have been added, for example, by a reviewing pathologist. FIG. 6 shows one example of a matched pair of an image of a HER2-IHC-stained slide (left) and an image of an H&E-stained slide (right), in which the image of HER2-IHC-stained slide has been annotated by two curves drawn in red. Pre-processing stage 390 may perform alignment and/or registration of the paired images before and/or after the images are divided into patches. Alignment may comprise designating one image as the reference image, also called the fixed image, and applying geometric transformations or local displacements to the other image so that the other image aligns with the reference image. Because the IHC images (i.e., the target images) provide the ground truth for training the network, it may be desired to designate the target images as the reference images for purposes of alignment and registration. Aligned pairs of patches from the source set and the target set are selected, and this process results in one or more pairwise subsets of images for training data. Pre-processing stage 390 may input the patch pairs to the GAN or cGAN to train the deep learning network.

With respect back to FIG. 3, pre-processing stage 390 may use augmentation to artificially expand the size of the pairwise subset of images 345a by creating modified versions of images in the datasets. Image data augmentation may be performed by creating transformed versions of images in the datasets that belong to the same class as the original image. Transforms include a range of operations from the field of image manipulation, such as shifts, flips, zooms, and the like. In some instances, the operations include random erasing, shifting, brightness, rotation, Gaussian blurring, and/or elastic transformation to ensure that the model 340 is able to perform under circumstances outside those available from the pairwise subset of images 345a.

The training process for model 340 includes selecting hyperparameters for the model 340 and performing iterative operations of inputting images from the pairwise subset of images 345a into the model 340 to find a set of model parameters (e.g., weights and/or biases) that minimizes one or more loss or error functions for the model 340 (e.g., a first loss function to train the discriminator to maximize the probability of the image training data and a second loss function to train the discriminator to minimize the probability of the generated image sampled from the generator and train the generator to maximize the probability that the discriminator assigns to its own generated image). The hyperparameters are settings that can be tuned or optimized to control the behavior of the model 340. Most models explicitly define hyperparameters that control different aspects of the models such as memory or cost of execution. However, additional hyperparameters may be defined to adapt a model to a specific scenario. For example, the hyperparameters may include the number of hidden units of a model, the learning rate of a model, the convolution kernel width, or the number of kernels for a model. Each iteration of training can involve finding a set of model parameters for the model 340 (configured with a defined set of hyperparameters) so that the value of the loss or error function using the set of model parameters is smaller than the value of the loss or error function using a different set of model parameters in a previous iteration. The loss or error function can be constructed to measure the difference between the outputs inferred using the models 340 and the ground truth target images using the labels 350.

Once the set of model parameters are identified, the model 340 has been trained and can be validated using the pairwise subset of images 345b (testing or validation data set). The validation process includes iterative operations of inputting images from the pairwise subset of images 345b into the model 340 using a validation technique such as K-Fold Cross-Validation, Leave-one-out Cross-Validation, Leave-one-group-out Cross-Validation, Nested Cross-Validation, or the like to tune the hyperparameters and ultimately find the optimal set of hyperparameters. Once the optimal set of hyperparameters are obtained, a reserved test set of images from the subset of images 345b are input into the model 345 to obtain output (in this example, generated images with characteristics similar to a target image), and the output is evaluated versus ground truth target images using correlation techniques such as Bland-Altman method and the Spearman's rank correlation coefficients and calculating performance metrics such as the error, accuracy, precision, recall, receiver operating characteristic curve (ROC), etc.

As should be understood, other training/validation mechanisms are contemplated and may be implemented within the computing environment 300. For example, the model 340 may be trained and hyperparameters may be tuned on images from the pairwise subset of images 345a and the images from the pairwise subset of images 345b may be used only for testing and evaluating performance of the model 340.

The model training stage 310 outputs trained models including one or more trained transformation models 360 and optionally one or more image analysis models 365. In some instances, a first model 360a is trained to process a source image 330 of a biological specimen. The source image 330 is an image of a section that has been stained with one or more selected histochemical stains. The source image 330 is obtained by a transformation controller 370 within the transformation stage 315. The transformation controller 370 includes program instructions for transforming, using the one or more trained transformation models 360, the source image 330 into a new image 375 having the characteristics of a target image. The characteristics of the target image are associated with an image of the section that has been stained with one or more selected IHC stains. The transformation includes: (i) inputting into a generator model (part of transformation model 360) a randomly generated noise vector and a latent feature vector from the source image 330 as input data; (ii) generating, by the generator model, a new image 375, (iii) inputting into a discriminator model (another part of model 360) the new image 375; and generating, by the discriminator model, a probability (e.g., a number between 1 and 0) for the new image 375 being authentic or fake, where authentic means the image has characteristics that are similar to the characteristics of the target image, and fake means the image does not have characteristics that are similar to the characteristics of the target image.

In some instances, the new image 375 is transmitted to an analysis controller 380 within the analysis stage 320. The analysis controller 380 includes program instructions for analyzing, using the one or more image analysis models 365, the biological sample within the new image 375; and outputting an analysis result 385 based on the analyzing. The analyzing of the biological sample within the new image 375 may comprise extracting measurements based on area within the new image 375, one or more cells within the new image 375, and/or objects in the new image 375 aside from cells. Area-based measurements may include the most basic assessments, for example, quantifying the areas (2-dimensional) of a certain stain (e.g., chemical or IHC stain), the area of fat vacuoles, or other events present on a slide. Cell-based measurements aim at identifying and enumerating objects, e.g. cells. This identification of individual cells enables subsequent assessment of subcellular compartments. Finally, algorithms can be utilized to assess events or objects present on tissue sections that may not be comprised of individual cells. In certain instances, the imaging analysis algorithms are configured to locate cells or subcellular structures, and provide a quantitative representation of cell staining, morphology, and/or architecture that can ultimately be used to support diagnosis and prediction. In some instances, the imaging analysis algorithms are configured specifically for analysis of images having characteristics of the target images (e.g., images of sections that have been IHC-stained). For example, the analysis of the new image 375 may include calculating, from the new image 375, a level of expression of an antigen that is targeted by the at least one IHC stain. In another example, the analysis of the new image 375 may include calculating, from the new image 375, a score that is based on such a level of expression (e.g., a HER2 score).

While not explicitly shown, it will be appreciated that the computing environment 300 may further include a developer device associated with a developer. Communications from a developer device to components of the computing environment 300 may indicate what types of input images are to be used for the models, a number and type of models to be used, hyperparameters of each model, for example, learning rate and number of hidden layers, how data requests are to be formatted, which training data is to be used (e.g., and how to gain access to the training data) and which validation technique is to be used, and/or how the controller processes are to be configured.

Figure 7:
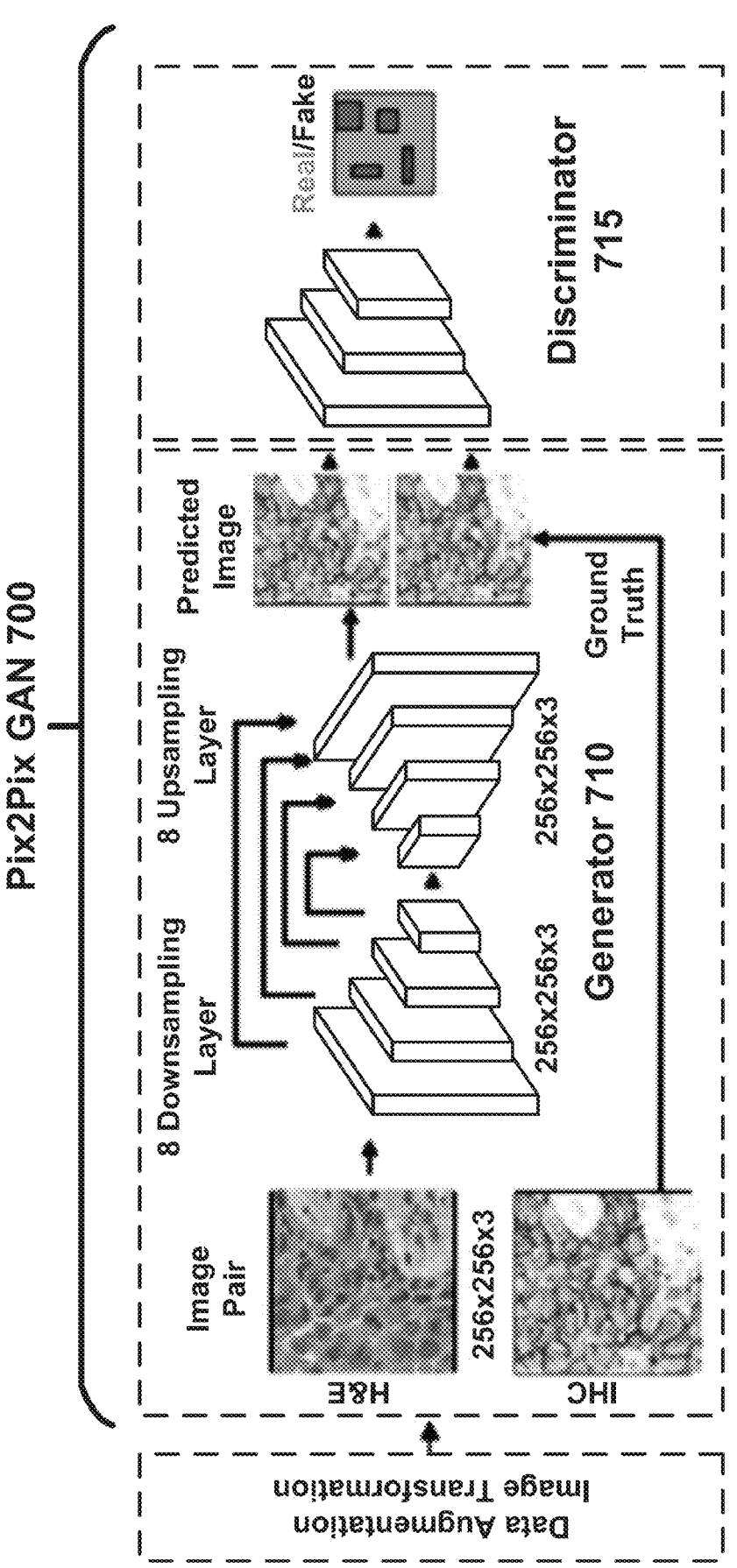
FIG. 7 shows an example of an implementation of a conditional GAN model that uses a Pix2Pix GAN according to some embodiments.

One particular example of a cGAN model 400 that may be used to train the generator network 410 is a Pix2Pix GAN. FIG. 7 shows an example of an implementation of cGAN model 400 that uses a Pix2Pix GAN 700 to train a generator network 710 to translate images of H&E-stained tumor sections into synthetic images of IHC-stained (e.g., HER2-

IHC-stained) tumor sections. As illustrated in FIG. 7, the generator network 710 is implemented using a U-Net architecture, which includes an encoder having layers that progressively downsample the input to a bottleneck layer, and a decoder having layers that progressively upsample the bottleneck output to produce the output. As shown in FIG. 7, the U-Net also includes skip connections between encoder and decoder layers having equally sized feature maps; these connections concatenate the channels of the feature map of the encoder layer with those of the feature map of the corresponding decoder layer. In a particular example, the generator network 710 is updated via L1 loss measured between the generated image and the expected output image (e.g., the "predicted image" and the "ground truth," respectively, in FIG. 7).

Figure 9:
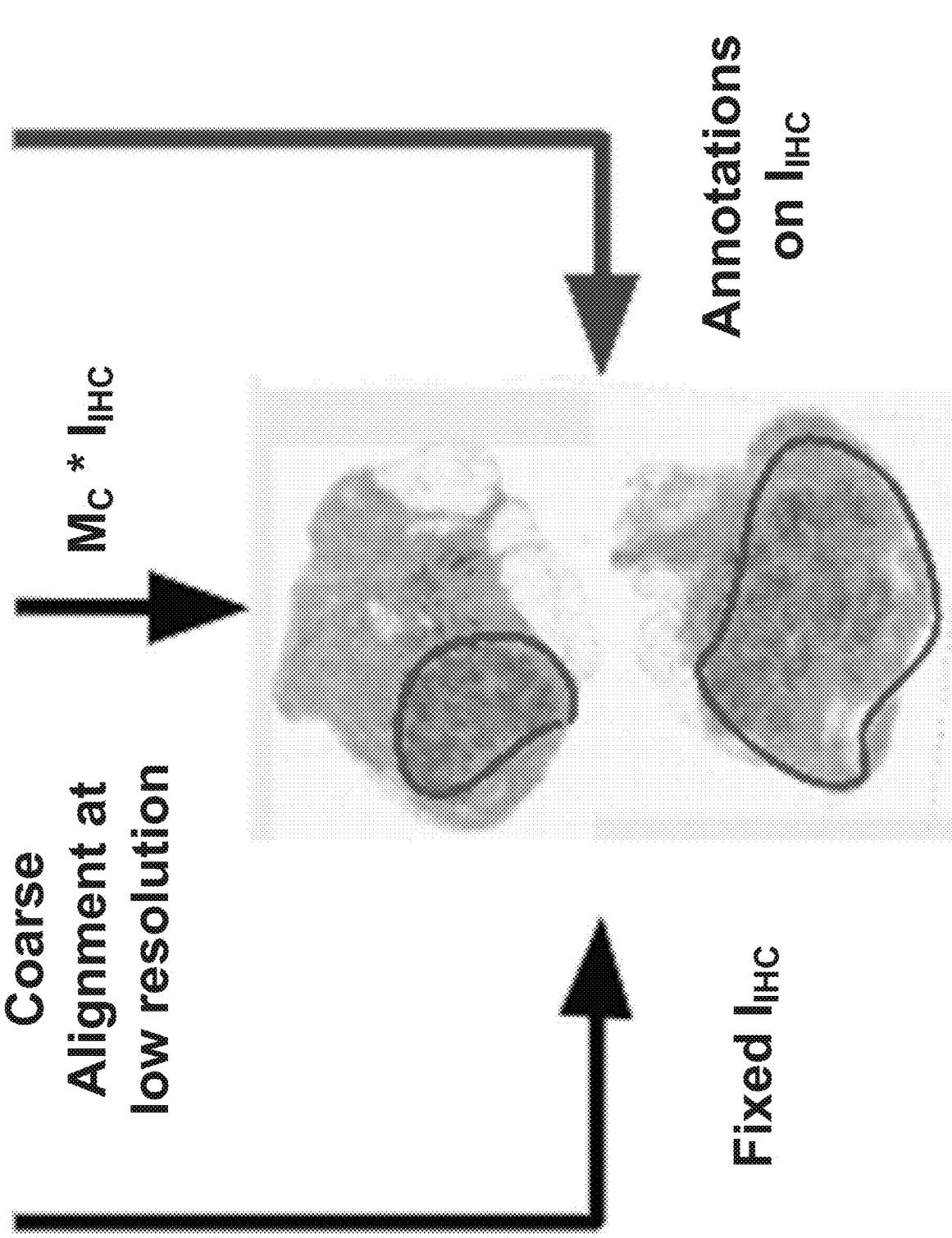
FIG. 9 shows an example of coarse alignment according to some embodiments.

Generally, use of a Pix2Pix GAN requires that the matched pairs of image patches that are to be used to train the generator network have been registered (e.g., at the pixel level). FIG. 8 illustrates a flowchart for an exemplary process 800 to produce matched and registered pairs of image patches from a matched image pair as described herein (e.g., for training and/or validation). Process 800 may be performed by pre-processing stage 390. Referring to FIG. 8, at block 804, low-resolution versions of the matched image pair are coarsely aligned. FIG. 9 shows an example of performing such coarse alignment by applying a transformation matrix Mc (e.g., including a translation and/or a rotation) to a low-resolution version of an image $I_{H\&E}$ of an H&E-stained section to align it to an annotated image $I_{IHC}$ of an IHC-stained section. Transformation matrix $M_C$ may be calculated automatically based on, for example, an outline of the tissue in each of the images to be aligned.

Figure 11:
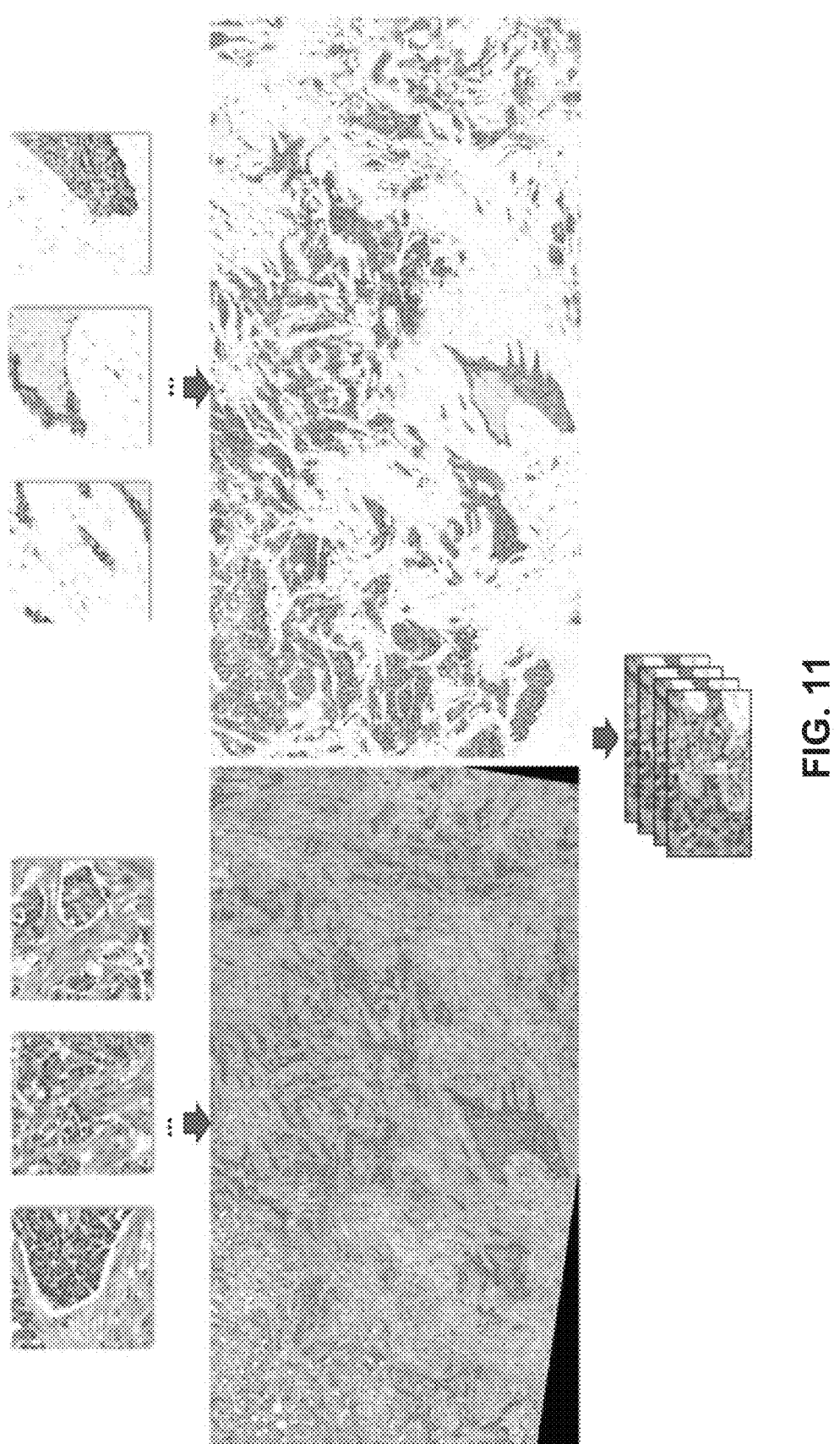
FIG. 11 a process of obtaining training data according to some embodiments.
Figure 12:
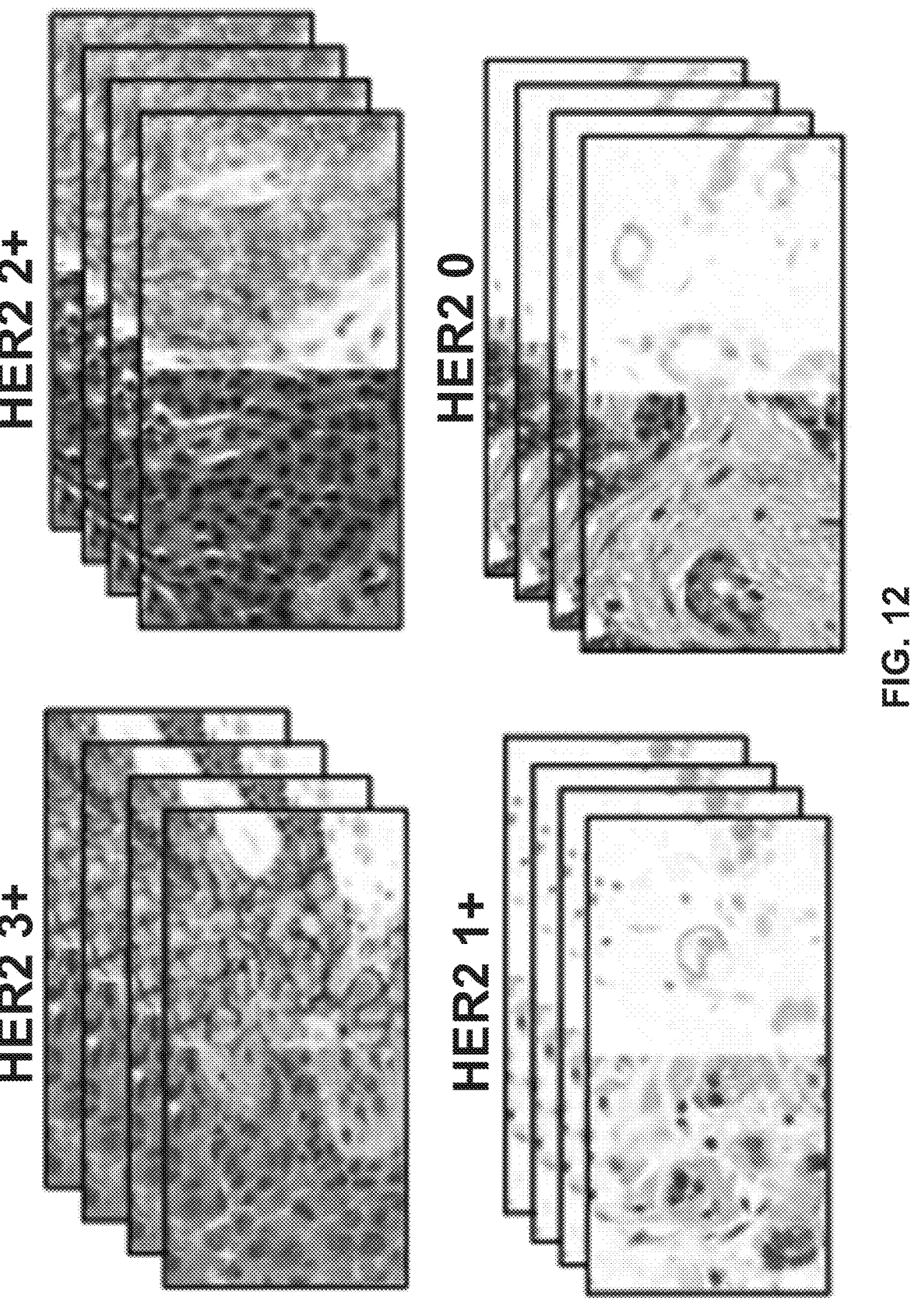
FIG. 12 shows an example of sets of training data according to some embodiments.

At block 808, tiles are extracted from regions of interest (ROIs) of the coarsely aligned image pair (e.g., by projecting a grid onto each image that covers the annotations, and extracting corresponding tiles from each image). FIG. 10 shows an example of a tile $P_{IHC}$ of size 2048×2048 pixels from an ROI of image $I_{IHC}$ and a corresponding tile $P_{H\&E}$ of size 2048×2048 pixels from image $I_{H\&E}$. At block 812, full-resolution versions of extracted tile pairs are finely aligned. Such fine alignment may include, for example, scaling, deskewing, and/or warping of a tile from one of the images (e.g., $I_{H\&E}$) to register it to the corresponding tile from the other image (e.g., $I_{IHC}$ (the reference image as discussed above)). At block 816, the finely aligned tiles are stitched together to obtain a registered image pair; at block 820, each of the registered images is sliced into patches (e.g., of size 128×128, 256×256, or another size); and at block 824, matched patches from each registered image are combined to obtain training images. FIG. 11 illustrates, from top to bottom, a process of stitching together finely-aligned tiles of each image to obtain a registered image pair, and combining matched patches from each of the registered images to obtain a set of training images. FIG. 12 shows an example of sets of training data for using a Pix2Pix GAN implementation to train generator network 410 to transform images of H&E-stained sections to synthetic images of HER-IHC-stained sections, in which each of the training images is labeled with the HER2 score of its component HER-IHC-stained patch.

Figure 13:
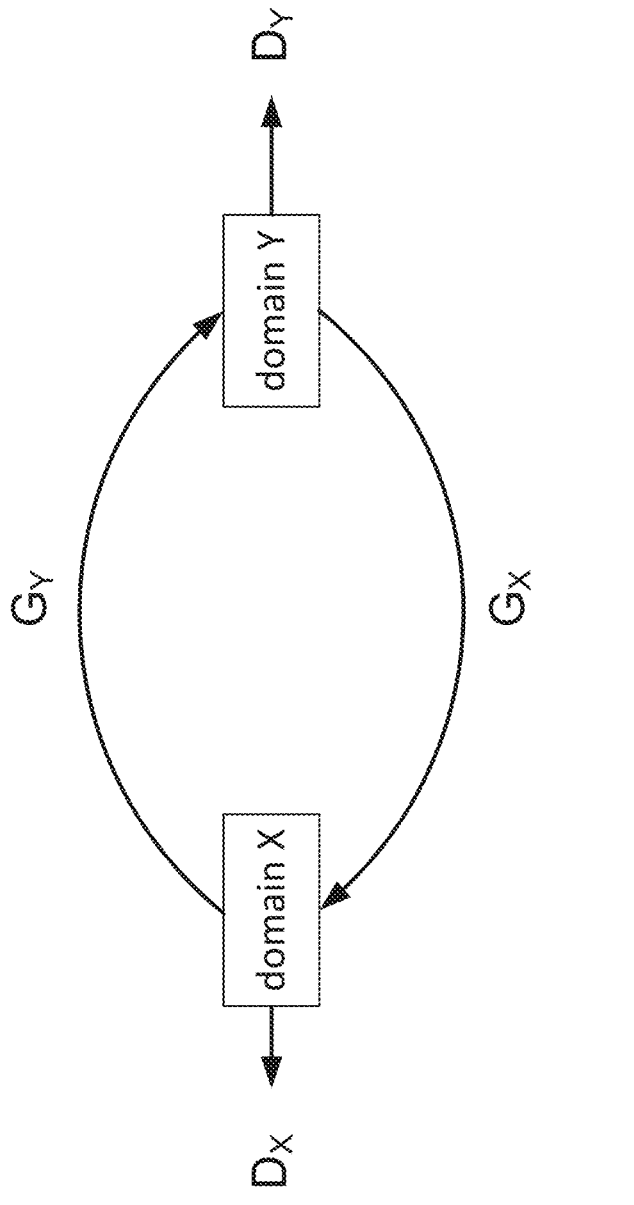
FIG. 13 shows a representation of networks and network connections in a Cycle-GAN according to some embodiments.

Another particular example of a cGAN model 400 that may be used to train the generator network 410 is a Cycle-GAN that includes multiple generator networks and multiple discriminator networks. FIG. 13 shows a representation of generator networks $G_X$ and $G_Y$ and discriminator networks $D_X$ and $D_Y$ in a Cycle-GAN. In this example, the Y domain corresponds to images depicting a sample that has been IHC-stained, and the X domain corresponds to images depicting a sample that has been histochemically stained.

Figure 14:
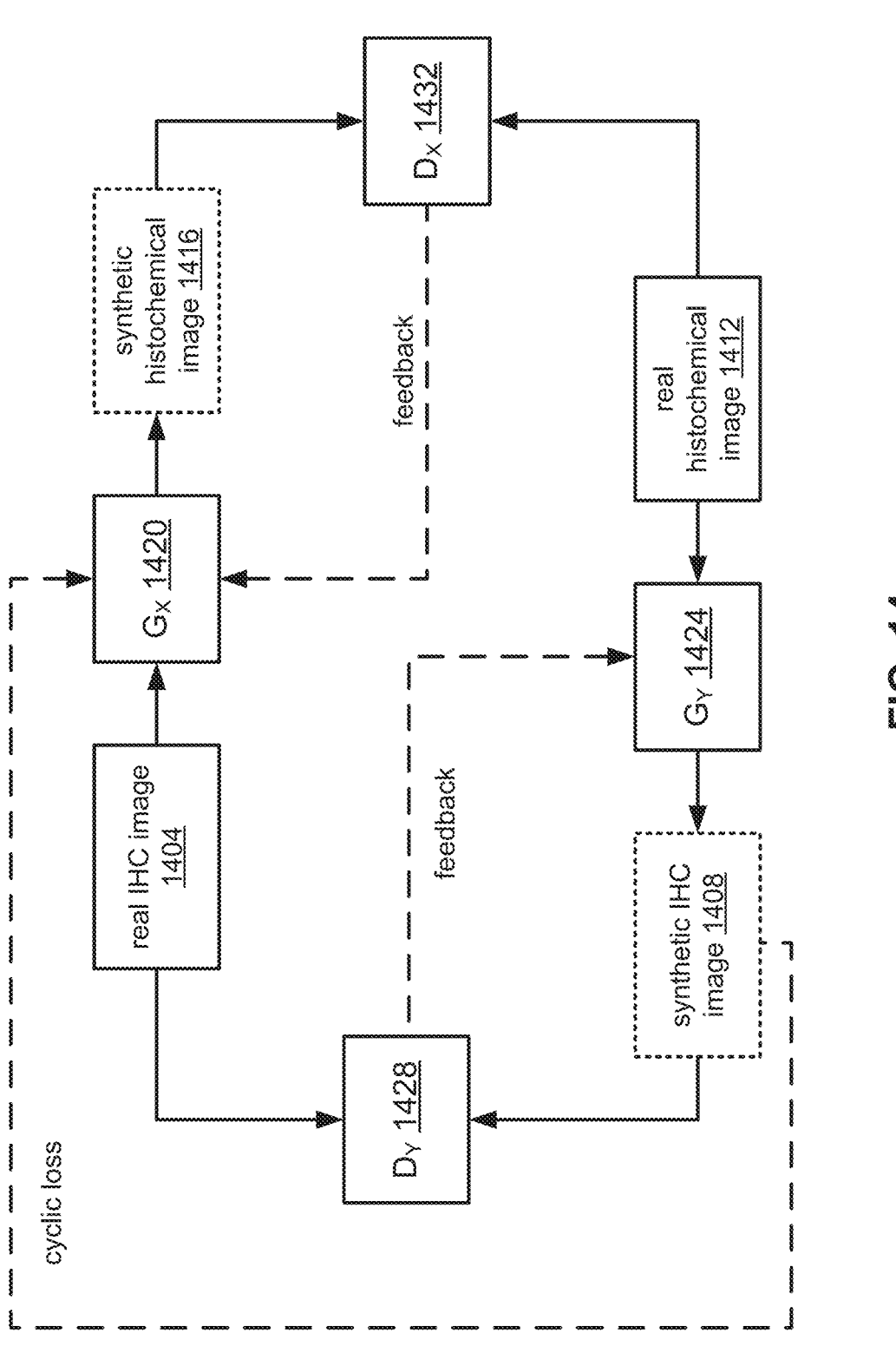
FIG. 14 illustrates a flow of generating and discriminating images using a Cycle-GAN according to some embodiments.
Figures 17A, 17B:
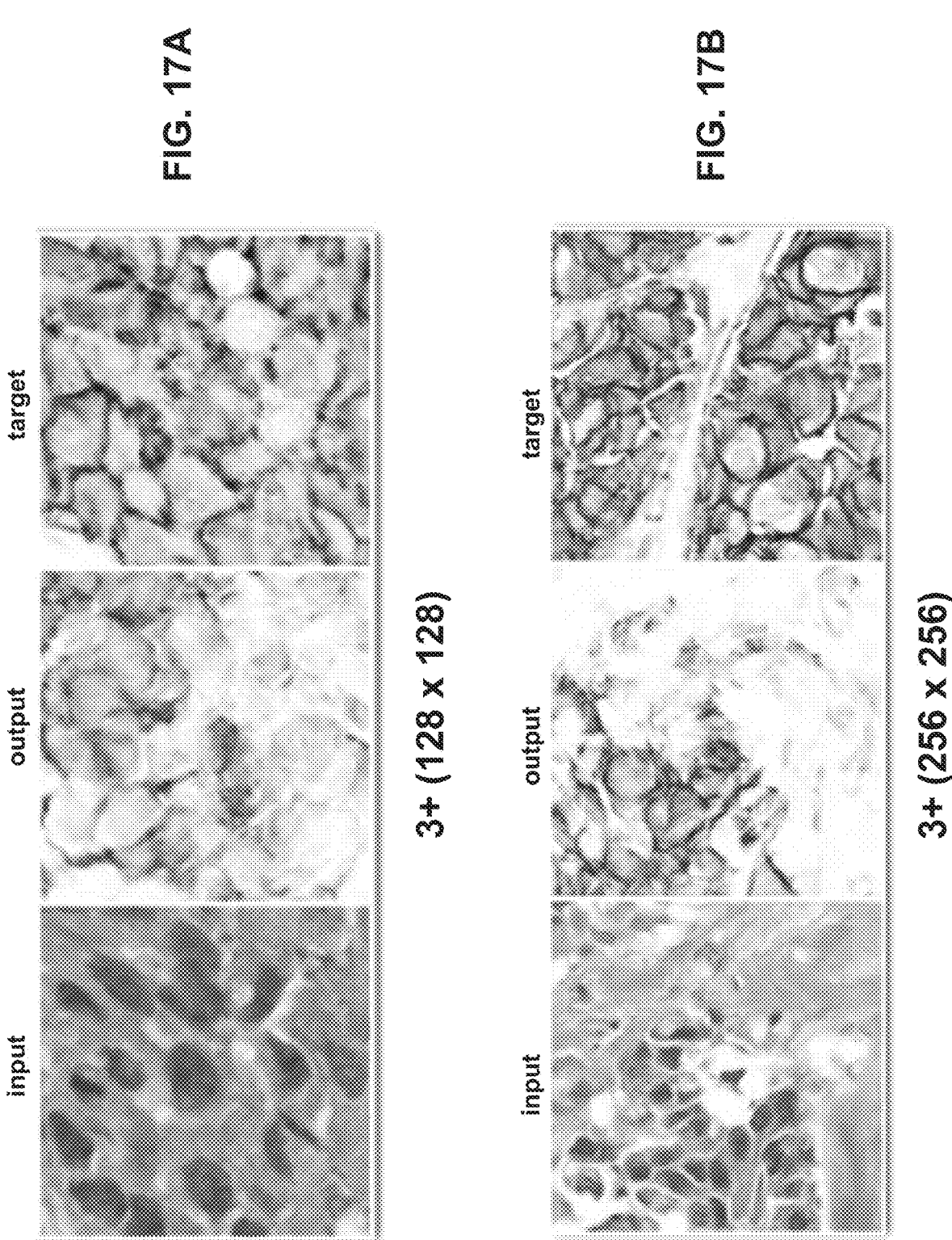
FIGS. 17A, 17B, 18A, 18B, 19A, 19B, 20A and 20B show examples of input images, target images, and output images generated according to various embodiments.
Figures 18A, 18B:
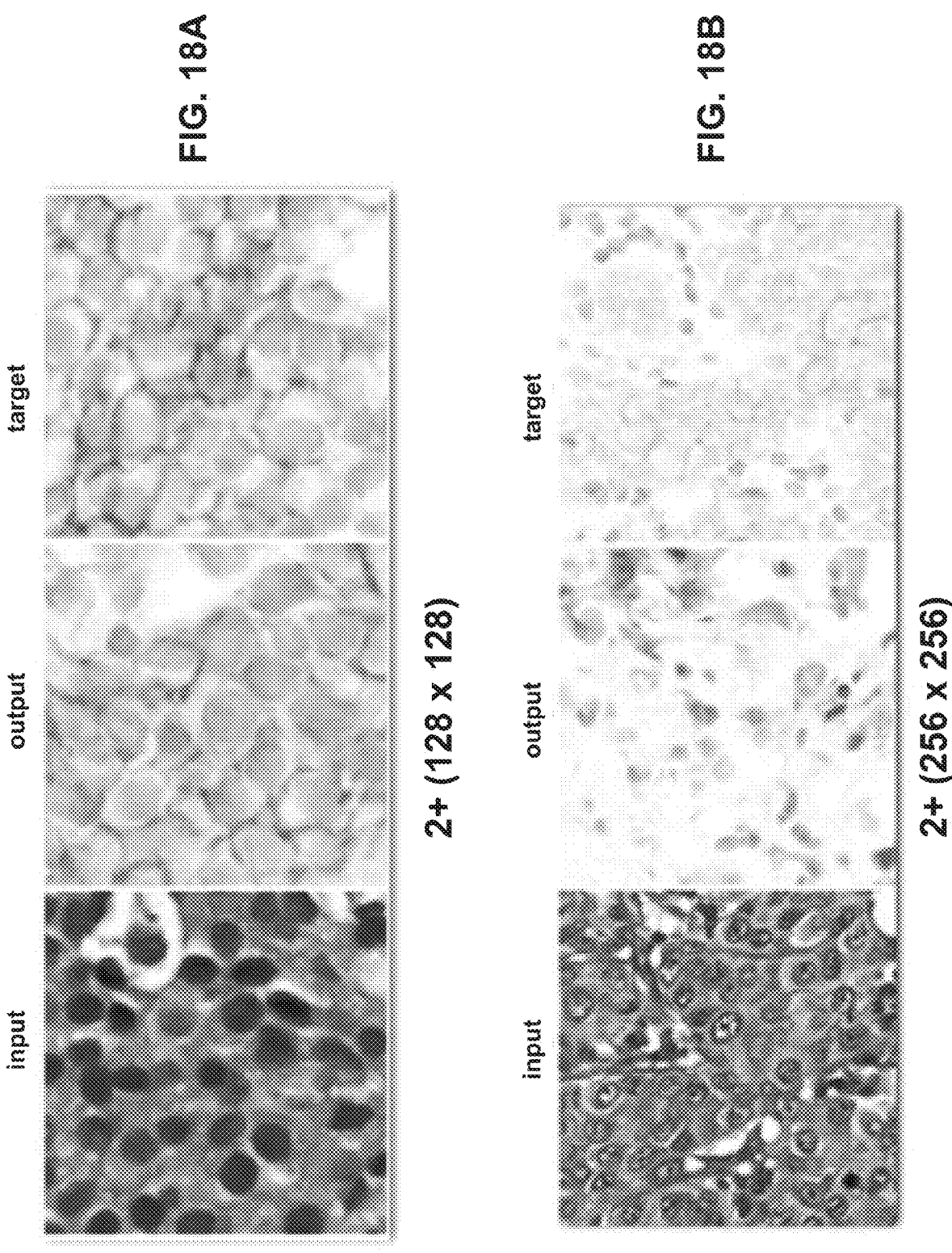
Figures 19A, 19B:
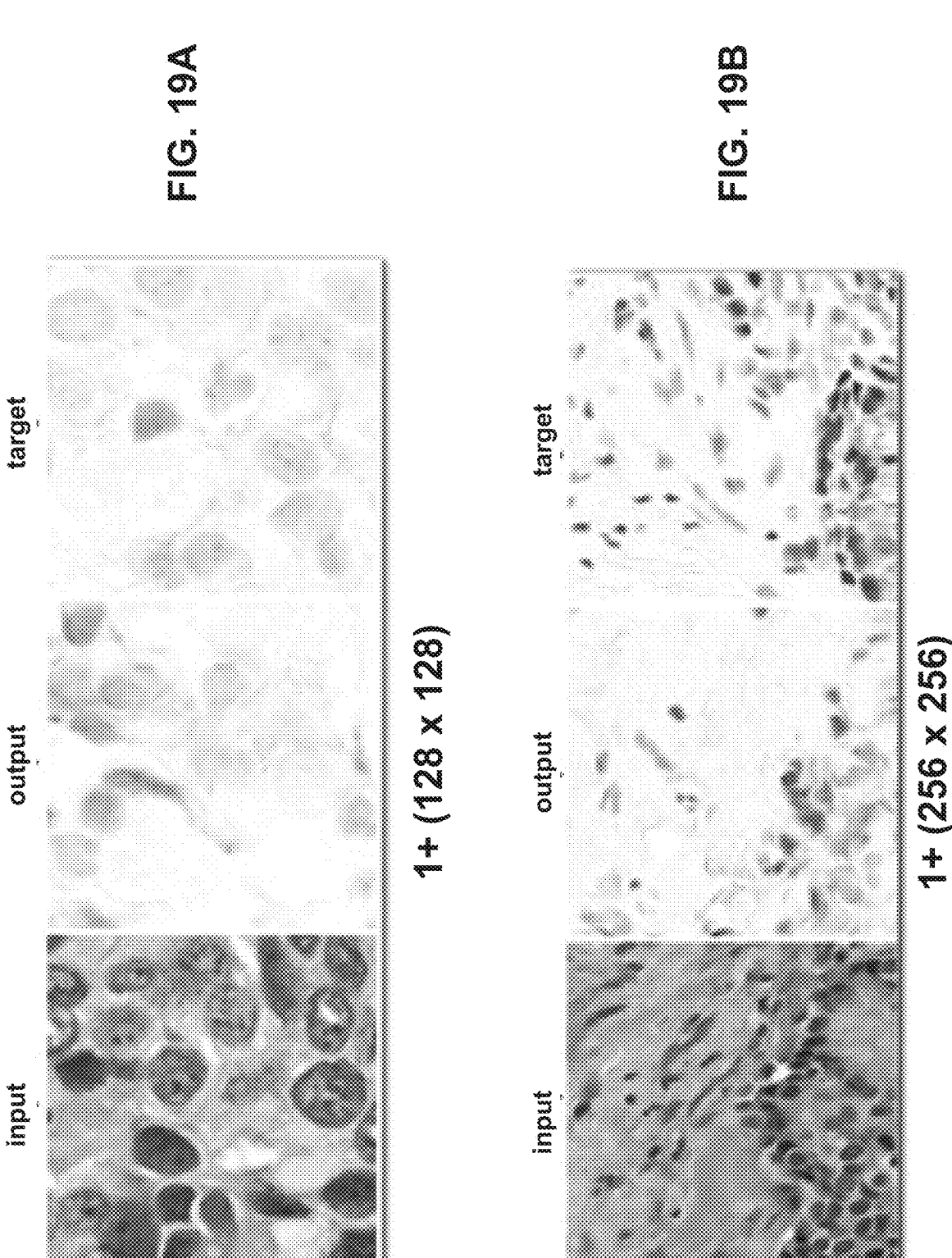
Figures 20A, 20B:
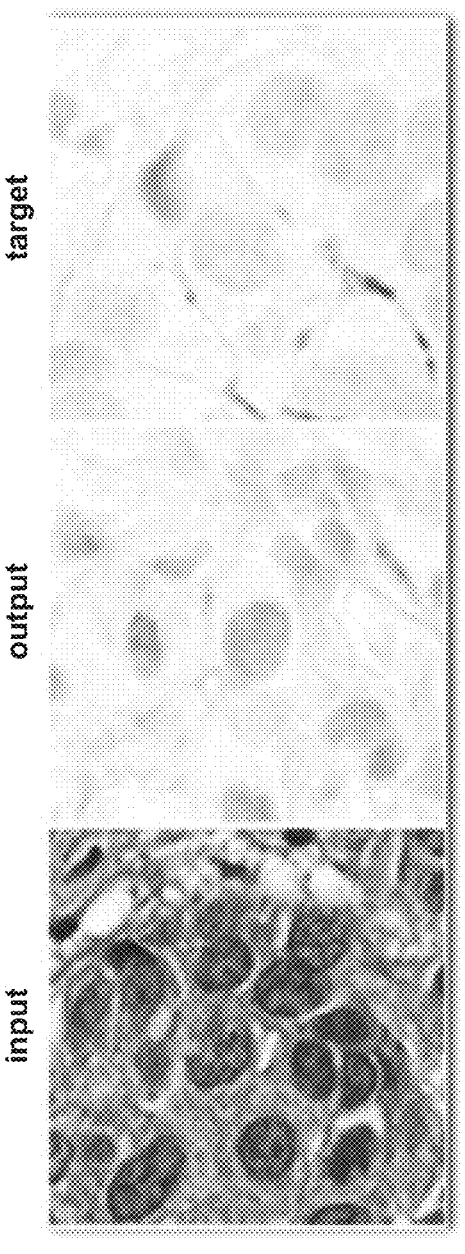

FIG. 14 illustrates a flow among the generator and discriminator networks in an application of a Cycle-GAN as described herein. The Cycle-GAN includes an X-to-Y generator network $G_Y$ 1424 (to be trained as generator network 410) and also includes a Y-to-X generator network $G_X$ 1420 that is configured and trained to transform an image of an IHC-stained sample to an image of a histochemically stained sample. The generator network $G_X$ 1420 can include one or more convolution layers and may include a U-net or a V-net. In some instances, the generator network $G_X$ 1420 includes a feature-extracting encoder, a transformer, and a decoder, each having one or more convolution layers. The architectures of the generator networks $G_X$ 1420 and $G_Y$ 1424 may be the same.

The Cycle-GAN includes a discriminator network $D_X$ 1432 that discriminates between real and fake images that depict a histochemically-stained sample (e.g., real histochemically-stained image 1412 and fake histochemically-stained image 1416) and another discriminator network $D_Y$ 1428 that discriminates between fake and real images that depict an IHC-stained sample (e.g., real IHC-stained image 1404 and fake IHC-stained image 1408). Each of the discriminator networks $D_X$ and $D_Y$ may include one or more convolution layers and an activation layer, and the architectures of the discriminator networks $D_X$ and $D_Y$ may be the same.

Use of a CycleGAN may have the advantage that fine registration of matched pairs of images (e.g., fine registration of images $I_{H\&E}$ and $I_{IHC}$ as described herein with reference to FIG. 8) is not required to generate the training data. However, better results were obtained when using a Pix2Pix GAN implementation to train generator network 410 on image patches of paired registered images.

Figures 15A, 15B:
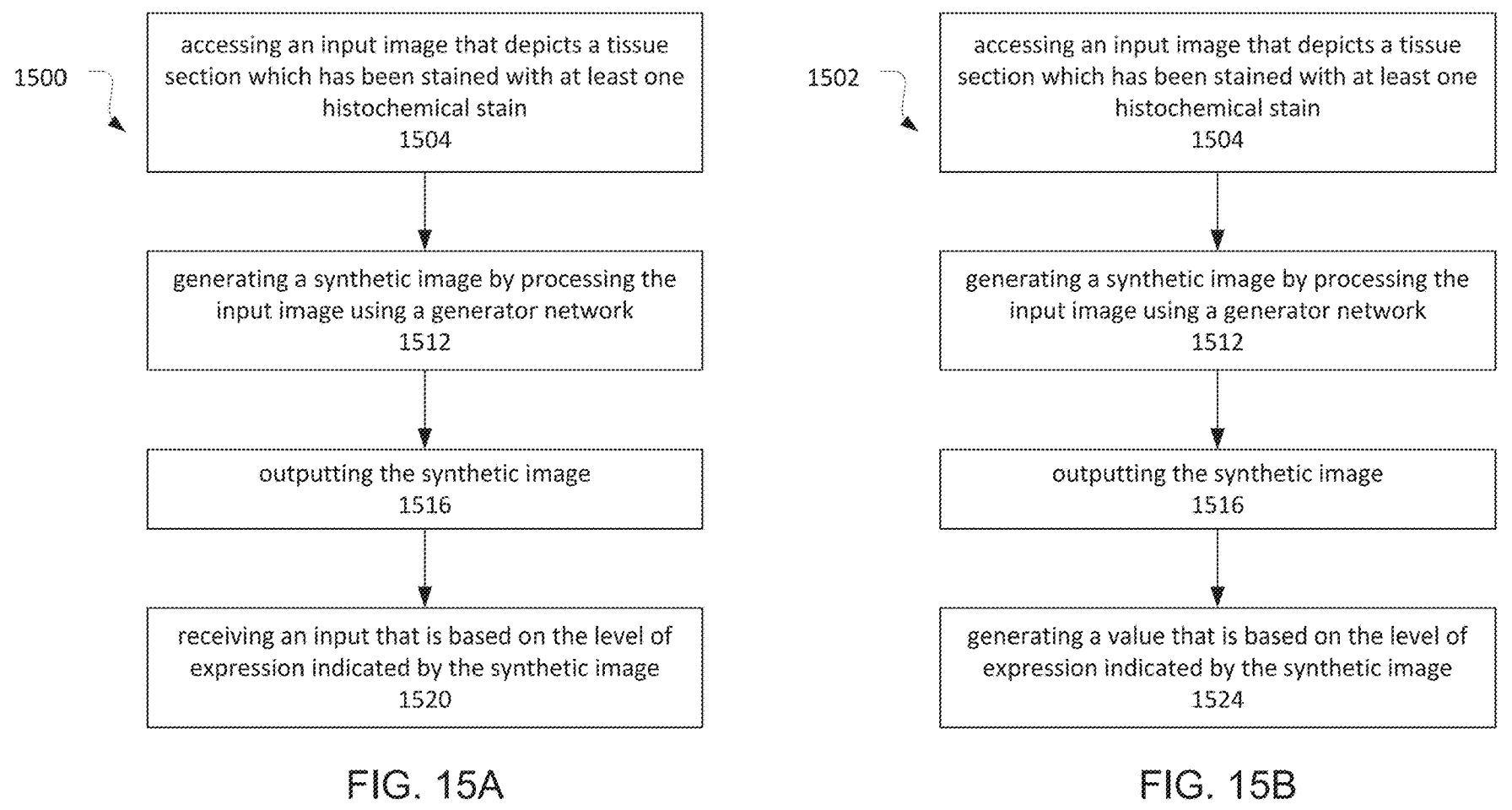

FIG. 15A illustrates a flowchart for an exemplary process 1500 to transform a source image (e.g., a source image from a set of source images to be processed) into a new image (e.g., a new image of a set of new images to be generated) having characteristics similar to a target image. Process 1500 may be performed using one or more computing systems, models, and networks (e.g., as described herein with respect to FIGS. 3, 4, and 7). With reference to FIG. 15A, at block 1504, an input image that depicts a tissue section which has been stained with at least one histochemical stain is accessed. At block 1512, a synthetic image is generated by processing the input image using a generator network. The synthetic image depicts a tissue section that has been stained with at least one IHC stain that targets a first antigen. The generator network has been trained using a training data set that includes a plurality of pairs of images, in which each pair includes an image of a first section of a tissue that has been stained with the at least one histochemical stain, and an image of a second section of the tissue that has been stained with the at least one IHC stain. At block 1516, the synthetic image is outputted. At block 1520, an input that is based on a level of expression of the first antigen depicted in the synthetic image is received. For example, the input may be received from a user via a keyboard, touchscreen, etc. In some embodiments, process 1500 also includes determining, from the synthetic image, a value that is based on the level of expression of the first antigen. The determining may be performed, for example, by a trained network.

FIG. 15B illustrates a flowchart for another exemplary process 1502 to transform a source image (e.g., a source image from a set of source images to be processed) into a new image (e.g., a new image of a set of new images to be generated) having characteristics similar to a target image. Process 1500 may be performed using one or more computing systems, models, and networks (e.g., as described herein with respect to FIGS. 3, 4, and 7). With reference to FIG. 15B, at block 1504, an input image that depicts a tissue section which has been stained with at least one histochemical stain is accessed. At block 1512, a synthetic image is generated by processing the input image using a generator network. The generator network has been trained using a training data set that includes a plurality of pairs of images. A level of expression of an antigen that is targeted by the at least one IHC stain is determined from the synthetic image. At block 1516, the synthetic image is outputted. At block 1524, a value that is based on a level of expression of the first antigen is generated from the synthetic image.

In some embodiments of process 1500 or 1502, the histochemical stain is hematoxylin and eosin.

In some embodiments of process 1500 or 1502, the first antigen is a tumor-associated antigen. For example, the first antigen may be human epidermal growth receptor 2 (HER2). In such case, the received input value and/or the generated value may be a HER2 score.

In some embodiments of process 1500 or 1502, the generator network was trained as part of a generative adversarial network (e.g., a cGAN, a Pix2Pix GAN, or a Cycle-GAN).

In some embodiments of process 1500 or 1502, for each pair of images of the plurality of pairs of images, the image of the first section is stitched to the image of the second section. In such case, for each pair of images of the plurality of pairs of images, the image of the first section may be registered with the image of the second section before being stitched to the image of the second section.

The methods according to the present disclosure may be implemented to transform images of histochemically stained samples, which may be readily available, into synthetic images of IHC-stained samples (which may be more difficult, costly, and/or time-consuming to obtain non-virtually). Such methods may be used, for example, to enable use of H&E and synthetic IHC data to assist a pathologist in the efficient diagnosis of a cancer (e.g., breast cancer) subtype. Such a method may be implemented as a key part of a fast screening process to identify samples in which a particular biomarker is expressed without performing an actual IHC staining. Moreover, such "virtual staining" technology can also be combined with other artificial intelligence (AI) technologies to enhance the authenticity of the AI system (e.g., to enhance explainability and truthfulness of the algorithm output). Even further, a method of image transformation as described herein may be used to generate a large amount of imaging data (e.g., a large number of synthetic HER2-IHC images) for algorithm verification and training, thereby reducing the cost and time of algorithm development.

Figure 16:
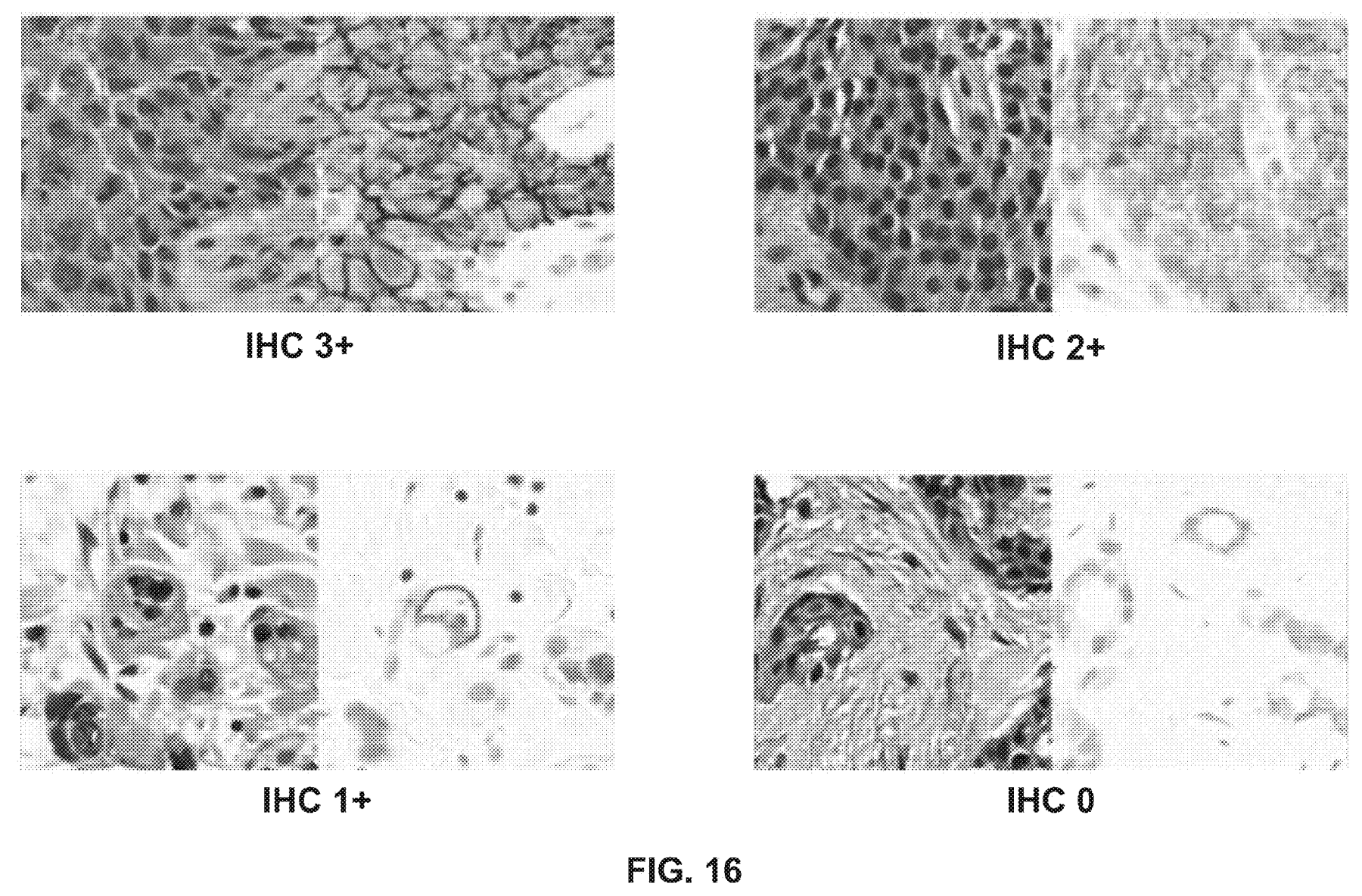

FIG. 16 shows an example, for each of the four HER2 scores as shown in the table above, of an actual matched pair of an image of a section of a tumor that has been H&E-stained and an image of a nearby section of the same tumor that has been HER2-IHC-stained and given the HER2 score shown. A Pix2Pix implementation of a system as described herein was trained and tested using 7,472 pairs of image patches of size 128×128 pixels using the four different HER2 scores. The Pix2Pix implementation was also trained and tested using 1,900 pairs of image patches of size 256×256 pixels using the four different HER2 scores. Training and testing datasets were divided to use 80% and 20%, respectively, and the parameters of the GAN network were Adam optimizer with a learning rate of 0.0002 and a number of epochs of 100 and 200, respectively.

FIGS. 17A and 17B, 18A and 18B, 19A and 19B, and 20A and 20B show input (H&E), target (HER-IHC), and output (synthetic HER-IHC) images for the two different image patch sizes for each of the four HER2 scores, respectively. In a test of randomly assembled real and synthetic HER-IHC images, it was demonstrated that the synthetic images were indistinguishable by a human pathologist from real HER-IHC images (percentage of test set that pathologists correctly identified as real or synthetic: 45.8%) and that the synthetic images can represent HER2 scores with different categories, especially strong HER2 intensity levels, with high concordance to a pathologist (consensus to pathologists 87.5%).

V. Additional Considerations

Some embodiments of the present disclosure include a system including one or more data processors. In some embodiments, the system includes a non-transitory computer readable storage medium containing instructions which, when executed on the one or more data processors, cause the one or more data processors to perform part or all of one or more methods and/or part or all of one or more processes disclosed herein. Some embodiments of the present disclosure include a computer-program product tangibly embodied in a non-transitory machine-readable storage medium, including instructions configured to cause one or more data processors to perform part or all of one or more methods and/or part or all of one or more processes disclosed herein.

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention as claimed has been specifically disclosed by embodiments and optional features, modification and variation of the concepts herein disclosed may be resorted to by those skilled in the art, and that such modifications and variations are considered to be within the scope of this invention as defined by the appended claim.

The description provides preferred exemplary embodiments only, and is not intended to limit the scope, applicability or configuration of the disclosure. Rather, the description of the preferred exemplary embodiments will provide those skilled in the art with an enabling description for implementing various embodiments. It is understood that various changes may be made in the function and arrangement of elements without departing from the spirit and scope as set forth in the appended claim.

Specific details are given in the following description to provide a thorough understanding of the embodiments. However, it will be understood that the embodiments may be practiced without these specific details. For example, circuits, systems, networks, processes, and other components may be shown as components in block diagram form in order not to obscure the embodiments in unnecessary detail. In other instances, well-known circuits, processes, algorithms, structures, and techniques may be shown without unnecessary detail in order to avoid obscuring the embodiments.

What is claimed is:

1. A method of image transformation, the method comprising:

accessing an input image that depicts a tissue section that has been stained with at least one histochemical stain;

generating a synthetic image by processing the input image using a generator network, the generator network having been trained using a training data set that includes a plurality of pairs of images corresponding to the tissue section, each pair comprising a histochemically stained image and an immunohistochemistry (IHC) stained image; and outputting the synthetic image; and performing one or more actions that include:

generating, from the synthetic image, a value derived from the synthetic image that represents a level of expression of a first antigen; and/or identifying a data point that is based on the level of expression of the first antigen from the synthetic image, wherein identifying the data point includes: receiving an input corresponding to the data point; and/or generating the data point, wherein the synthetic image depicts a tissue section that has been stained with at least one immunohistochemistry stain (IHC stain) that targets the first antigen, and wherein, for each pair of images of the plurality of pairs of images, the pair includes:

an image of a first section of a tissue that has been stained with the at least one histochemical stain, and an image of a second section of the tissue that has been stained with the at least one IHC stain, and the image of the first section is registered with the image of the second section.

2. The method of claim 1, wherein the one or more actions include identifying the data point, and wherein identifying the data point includes receiving the input, wherein the input includes a human epidermal growth receptor 2 (HER2) score.

3. The method of claim 1, wherein the one or more actions include identifying the data point, and wherein the method further comprises determining, from the synthetic image, a value that is based on the level of expression of the first antigen.

4. The method of claim 3, wherein the determining is performed by a trained network.

5. The method of claim 3, wherein the determined value is a human epidermal growth receptor 2 (HER2) score.

6. The method of claim 1, wherein the one or more actions includes generating and the value, and wherein generated value is a human epidermal growth receptor 2 (HER2) score.

7. The method of claim 1, wherein the histochemical stain is hematoxylin and eosin.

8. The method of claim 1, wherein the first antigen is a tumor-associated antigen.

9. The method of claim 8, wherein the first antigen is human epidermal growth receptor 2 (HER2).

10. The method of claim 1, wherein the generator network was trained as part of a generative adversarial network.

11. The method of claim 1, wherein, for each pair of images of the plurality of pairs of images, the image of the first section is stitched to the image of the second section.

12. The method of claim 1, wherein the histochemical stain does not include any antibody.

13. The method of claim 1, wherein all reagents in the histochemical stain have a molecular weight of 100 kilodaltons or less.

14. The method of claim 1, wherein all reagents in the histochemical stain have a molecular weight of 5 kilodaltons or less.

15. The method of claim 1, wherein all reagents in the histochemical stain have a molecular weight of 2 kilodaltons or less.

16. The method of claim 1, wherein the synthetic image is indistinguishable by a human observer from an image that depicts a tissue section which has actually been stained with the at least one IHC stain.

17. The method of claim 1, wherein the generator network is implemented as a U-Net.

18. The method of claim 1, wherein the generator network is implemented as an encoder decoder network.

19. The method of claim 1, wherein the generator network is updated via L1 loss measured between an image by the generator network and an expected output image.

20. The method of claim 1, further comprising: determining, by a user, a diagnosis of a subject based on the synthetic image.

21. The method of claim 20, further comprising administering, by the user, a treatment with a compound based on (i) the synthetic image, and/or (ii) the diagnosis of the subject.

22. A system comprising:

one or more data processors; and a non-transitory computer readable storage medium containing instructions which, when executed on the one or more data processors, cause the one or more data processors to perform a set of operations including:

accessing an input image that depicts a tissue section that has been stained with at least one histochemical stain;

generating a synthetic image by processing the input image using a generator network, the generator network having been trained using a training data set that includes a plurality of pairs of images; and outputting the synthetic image; and performing one or more actions that include:

generating, from the synthetic image, a value that is based on a level of expression of a first antigen; and/or identifying a data point that is based on the level of expression of the first antigen from the synthetic image, wherein identifying the data point includes:

receiving an input corresponding to the data point; and/or generating the data point, wherein the synthetic image depicts a tissue section that has been stained with at least one immunohistochemistry stain (IHC stain) that targets the first antigen, and wherein, for each pair of images of the plurality of pairs of images, the pair includes:

an image of a first section of a tissue that has been stained with the at least one histochemical stain, and an image of a second section of the tissue that has been stained with the at least one IHC stain, and the image of the first section is registered with the image of the second section.

23. A computer-program product tangibly embodied in a non-transitory machine-readable storage medium, including instructions configured to cause one or more data processors to perform a set of operations including:

accessing an input image that depicts a tissue section that has been stained with at least one histochemical stain;

generating a synthetic image by processing the input image using a generator network, the generator network having been trained using a training data set that includes a plurality of pairs of images; and outputting the synthetic image; and performing one or more actions that include:

generating, from the synthetic image, a value that is based on a level of expression of a first antigen; and/or identifying a data point that is based on the level of expression of the first antigen from the synthetic image, wherein identifying the data point includes:

receiving an input corresponding to the data point; and/or generating the data point, wherein the synthetic image depicts a tissue section that has been stained with at least one immunohistochemistry stain (IHC stain) that targets the first antigen, and wherein, for each pair of images of the plurality of pairs of images, the pair includes:

an image of a first section of a tissue that has been stained with the at least one histochemical stain, and an image of a second section of the tissue that has been stained with the at least one IHC stain, and the image of the first section is registered with the image of the second section.

*   *   *   *   *